(12) United States Patent
Park et al.

(10) Patent No.: US 10,693,081 B2
(45) Date of Patent: Jun. 23, 2020

(54) HETEROCYCLIC COMPOUND AND ORGANIC SOLAR CELL COMPRISING SAME

(71) Applicant: LG CHEM, LTD., Seoul (KR)

(72) Inventors: Junghyun Park, Daejeon (KR); Hang Ken Lee, Daejeon (KR); Donggu Lee, Daejeon (KR); Jaesoon Bae, Daejeon (KR); Jaechol Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 154 days.

(21) Appl. No.: 15/547,310

(22) PCT Filed: Feb. 17, 2016

(86) PCT No.: PCT/KR2016/001617
§ 371 (c)(1),
(2) Date: Jul. 28, 2017

(87) PCT Pub. No.: WO2016/133368
PCT Pub. Date: Aug. 25, 2016

(65) Prior Publication Data
US 2018/0026200 A1  Jan. 25, 2018

(30) Foreign Application Priority Data
Feb. 17, 2015 (KR) ........................ 10-2015-0024278

(51) Int. Cl.
*H01L 51/00* (2006.01)
*C07D 495/04* (2006.01)
(Continued)

(52) U.S. Cl.
CPC ........ *H01L 51/0068* (2013.01); *C07D 409/14* (2013.01); *C07D 417/14* (2013.01);
(Continued)

(58) Field of Classification Search
CPC ..... H01L 51/0034–0039; H01L 51/424–4253; C07D 409/00–14;
(Continued)

(56) References Cited

U.S. PATENT DOCUMENTS 9,184,392 B2    11/2015  Kim et al.
2012/0298976 A1*  11/2012  Sonar ................... C07D 285/14
                                                    257/40
(Continued)

FOREIGN PATENT DOCUMENTS

CN        104045812       9/2014
KR     10-2013-0090736 A    8/2013
(Continued)

OTHER PUBLICATIONS

Zhou, et al. "Solution-processed and high-performance organic solar cells using small molecules with a benzodithiophene unit." Journal of the American Chemical Society 135.23 (2013): 8484-8487.*

(Continued)

*Primary Examiner* — William E McClain
(74) *Attorney, Agent, or Firm* — Myers Bigel, P.A.

(57) ABSTRACT

The present specification relates to a heterocyclic compound and an organic solar cell including the same.

15 Claims, 6 Drawing Sheets

(51) Int. Cl.
*C07D 409/14* (2006.01)
*C07D 417/14* (2006.01)
*H01L 51/42* (2006.01)

(52) U.S. Cl.
CPC ........ *C07D 495/04* (2013.01); *H01L 51/0074* (2013.01); *H01L 51/42* (2013.01); *H01L 51/424* (2013.01); *H01L 51/4253* (2013.01); *Y02E 10/549* (2013.01)

(58) Field of Classification Search
CPC .... C07D 413/00–14; C07D 417/00–14; C07D 419/00–14
See application file for complete search history.

(56) References Cited

U.S. PATENT DOCUMENTS

| | | | |
|---|---|---|---|
| 2014/0142308 A1* | 5/2014 | Chen | C07D 333/22 544/296 |
| 2014/0166942 A1* | 6/2014 | Izawa | H01L 51/0036 252/511 |
| 2014/0290747 A1 | 10/2014 | Kim et al. | |
| 2015/0108409 A1* | 4/2015 | Meyer | C07D 495/04 252/500 |
| 2016/0194439 A1 | 7/2016 | Qin et al. | |

FOREIGN PATENT DOCUMENTS

| | | |
|---|---|---|
| KR | 10-2013-0090736 A1 | 8/2013 |
| KR | 1020160089859 | 7/2016 |
| WO | 2015-013747 A1 | 2/2015 |

OTHER PUBLICATIONS

Zhou, et al. "Small molecules based on benzo [1, 2-b: 4, 5-b'] dithiophene unit for high-performance solution-processed organic solar cells." Journal of the American Chemical Society 134.39 (2012): 16345-16351.*
Journal of Materials Chemistry A, vol. 2014, 2, pp. 1869-1876 (Nov. 25, 2013).
"A New Solution-Processed Diketopyrrolopyrrole Donor for Non-Fullerene Small-Molecule Solar Cells"; Chen, et al.; J.Mater.Chem. A,2013,2,1869-1876.
"Tuning Morphology and Photovoltaic Properties of Diketopyrrolopyrrole-Based Small-Molecule Solar Cells by Taloring End-Capped Aromatic Groups"; Zhang, et al.; Physical Chemistry Chemical 2014,16,4664.
"Phenyl-1,3,5-Trithienyl-Diketopyrrolopyrrole: A Molecular Backbone Potentially Affording High Efficiency for Solution-Processed Small Molecule Organic Solar Cells Through Judicious Molecular Design"; Zhang, et al.; Chem Asian Journal,2013,16,10,4664-4671.
Chung et al. "Highly Conjugated Side-Chain-Substituted Benzo [1,2-b:4,5-b']dithiophene-Based Conjugated Polymers for Use in Polymer Solar Cells" Macromolecules 47(1):97-105 (Jan. 14, 2014).
Extended European Search Report corresponding to European Patent Application No. 16752698.7 dated Jun. 13, 2018. (7 pages).

* cited by examiner

[Figure 1]
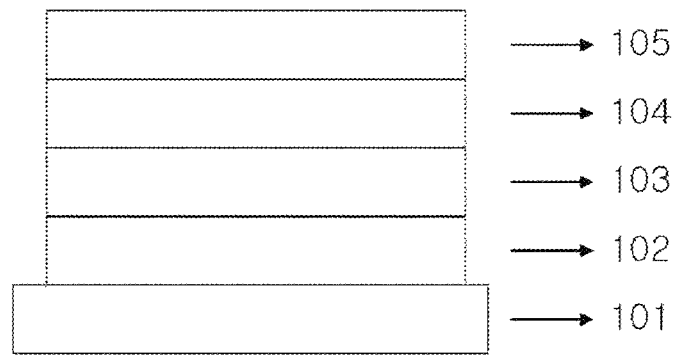

[Figure 2]
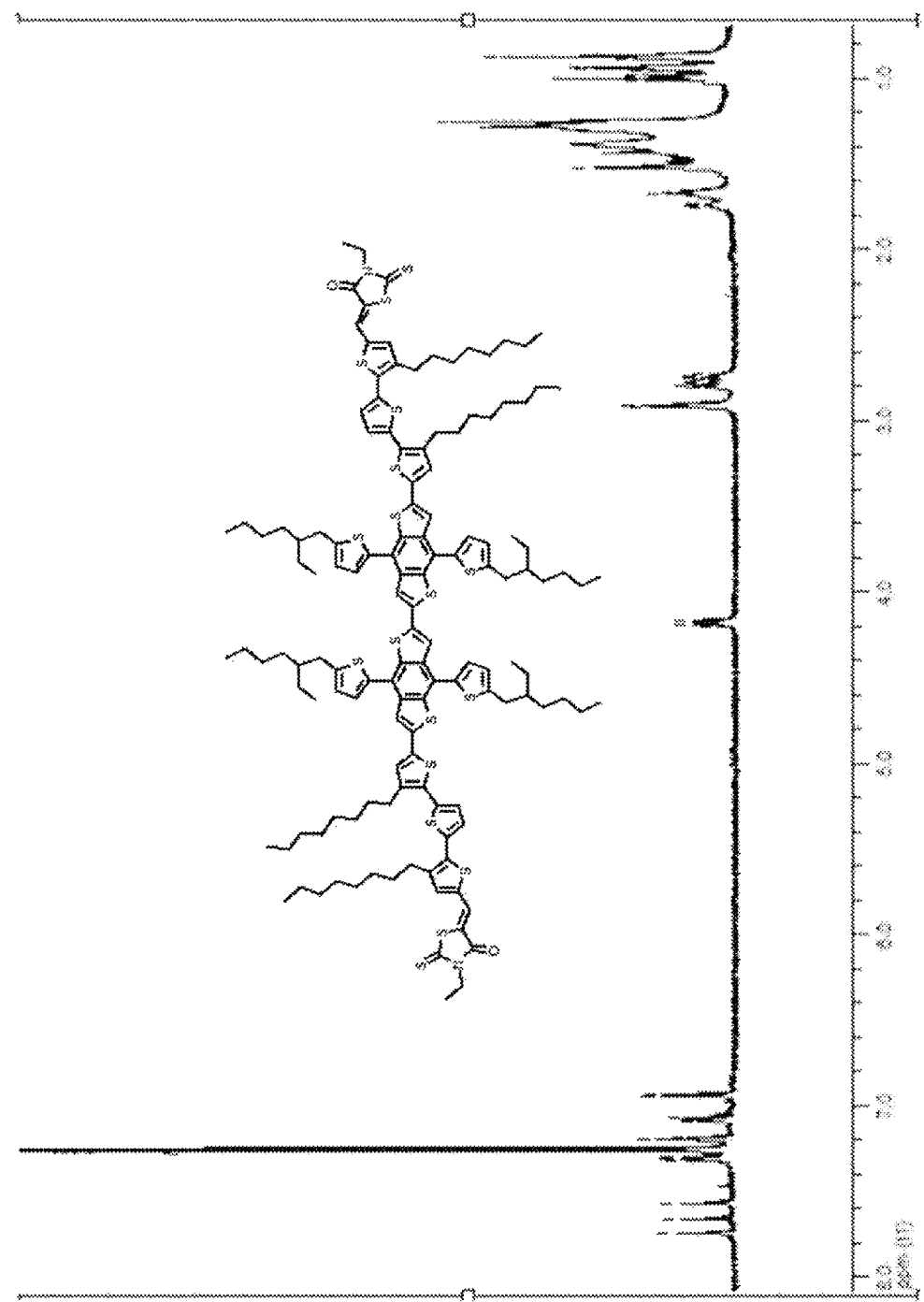

[Figure 3]
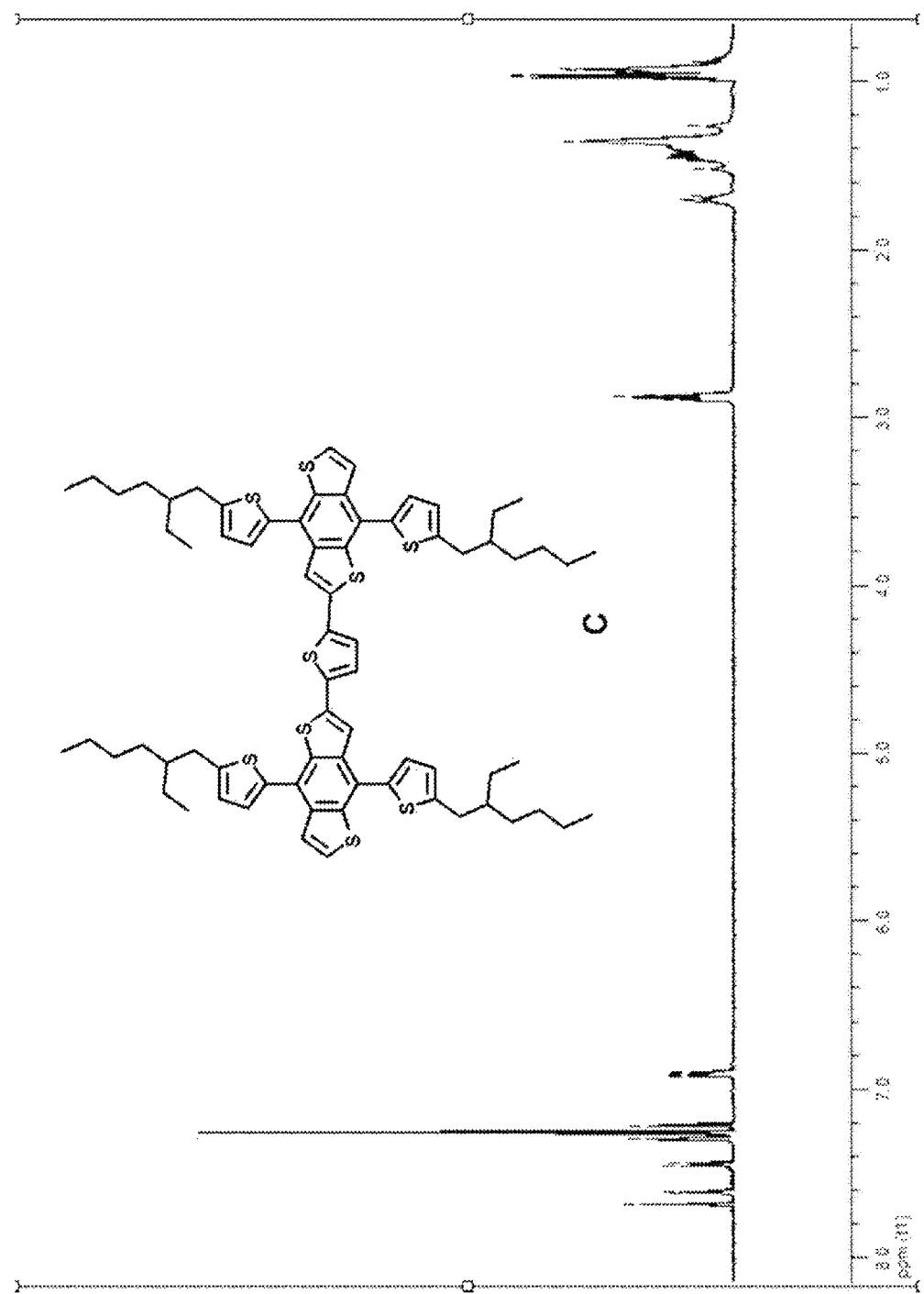

[Figure 4]
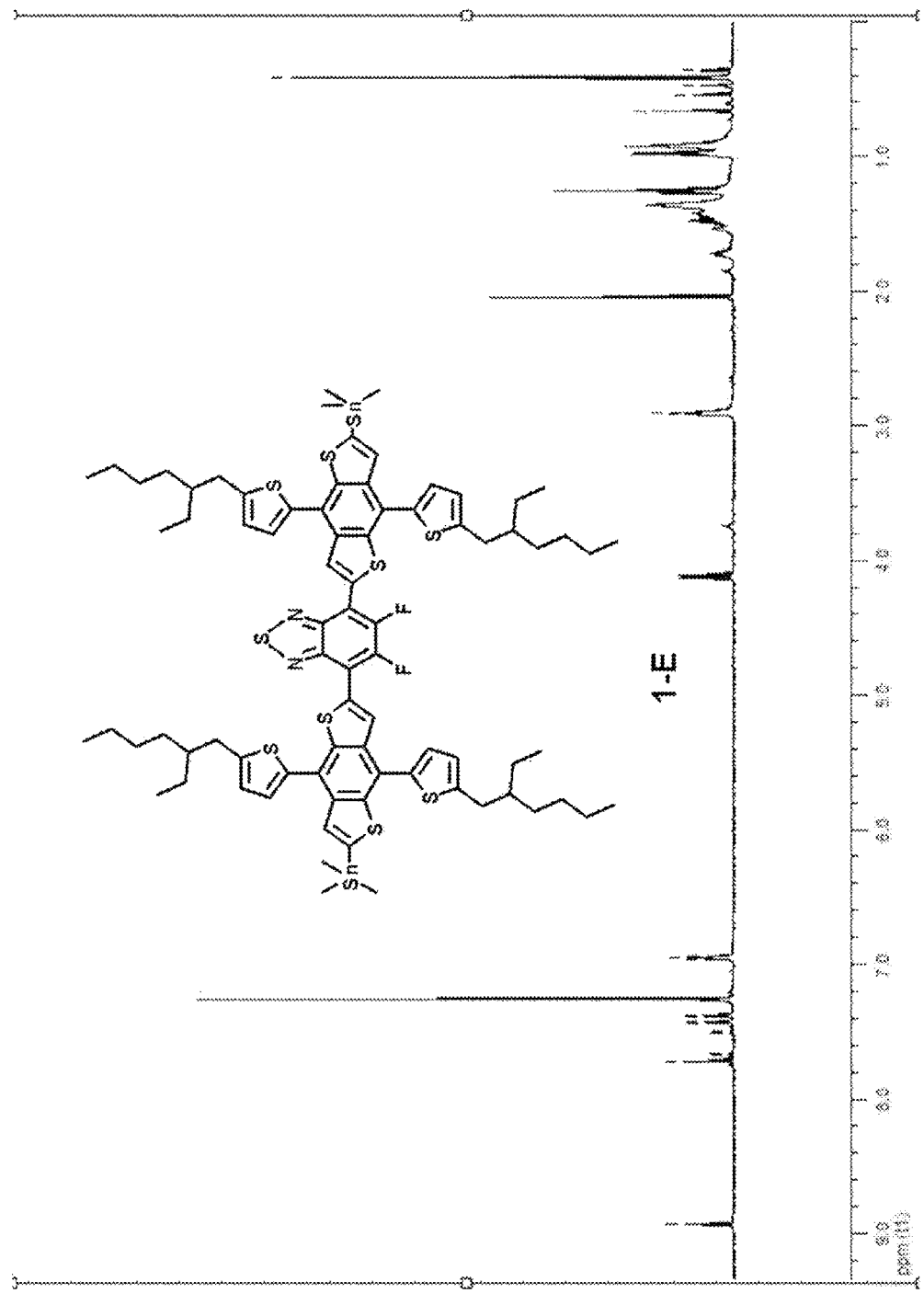

[Figure 5]
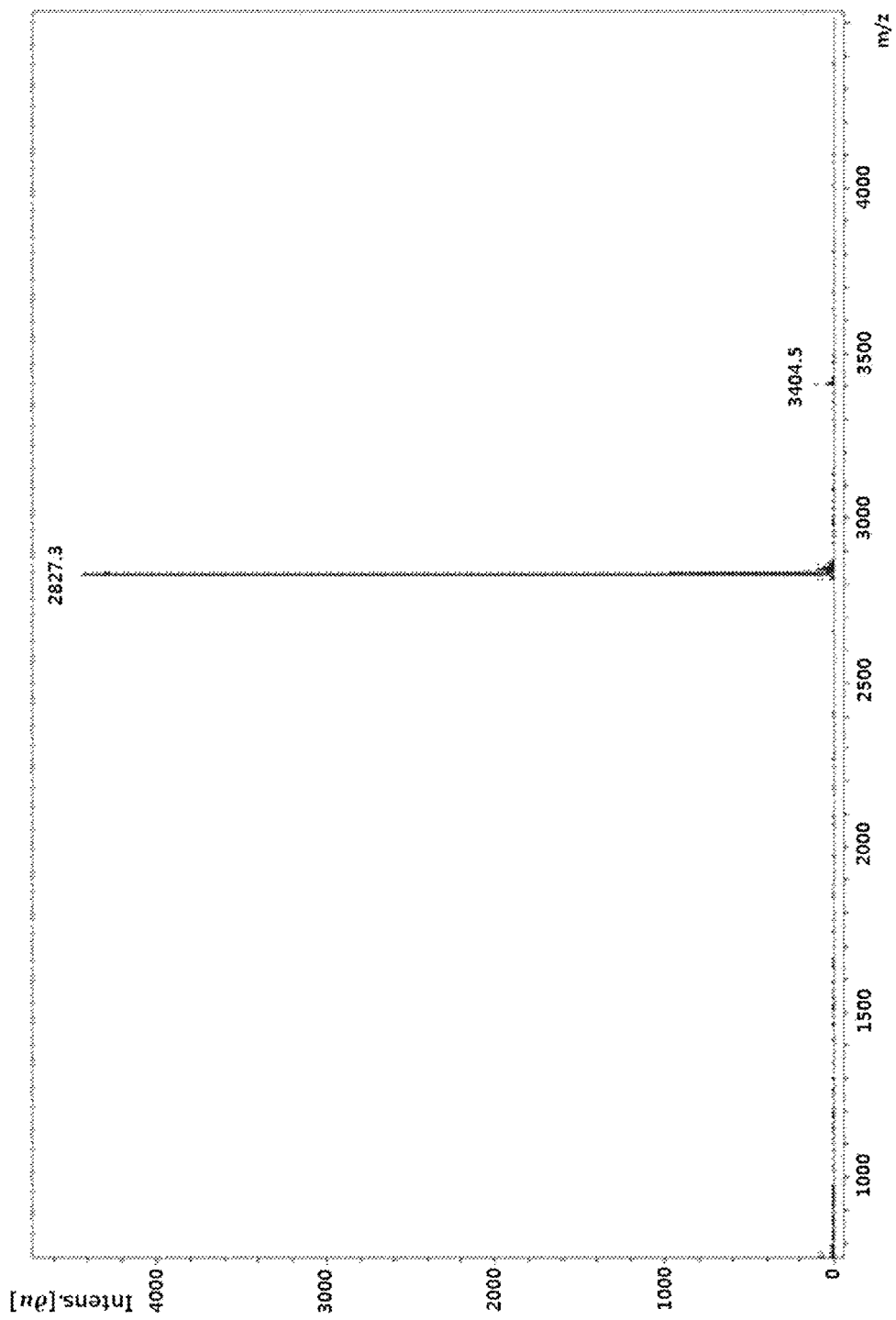

[Figure 6]
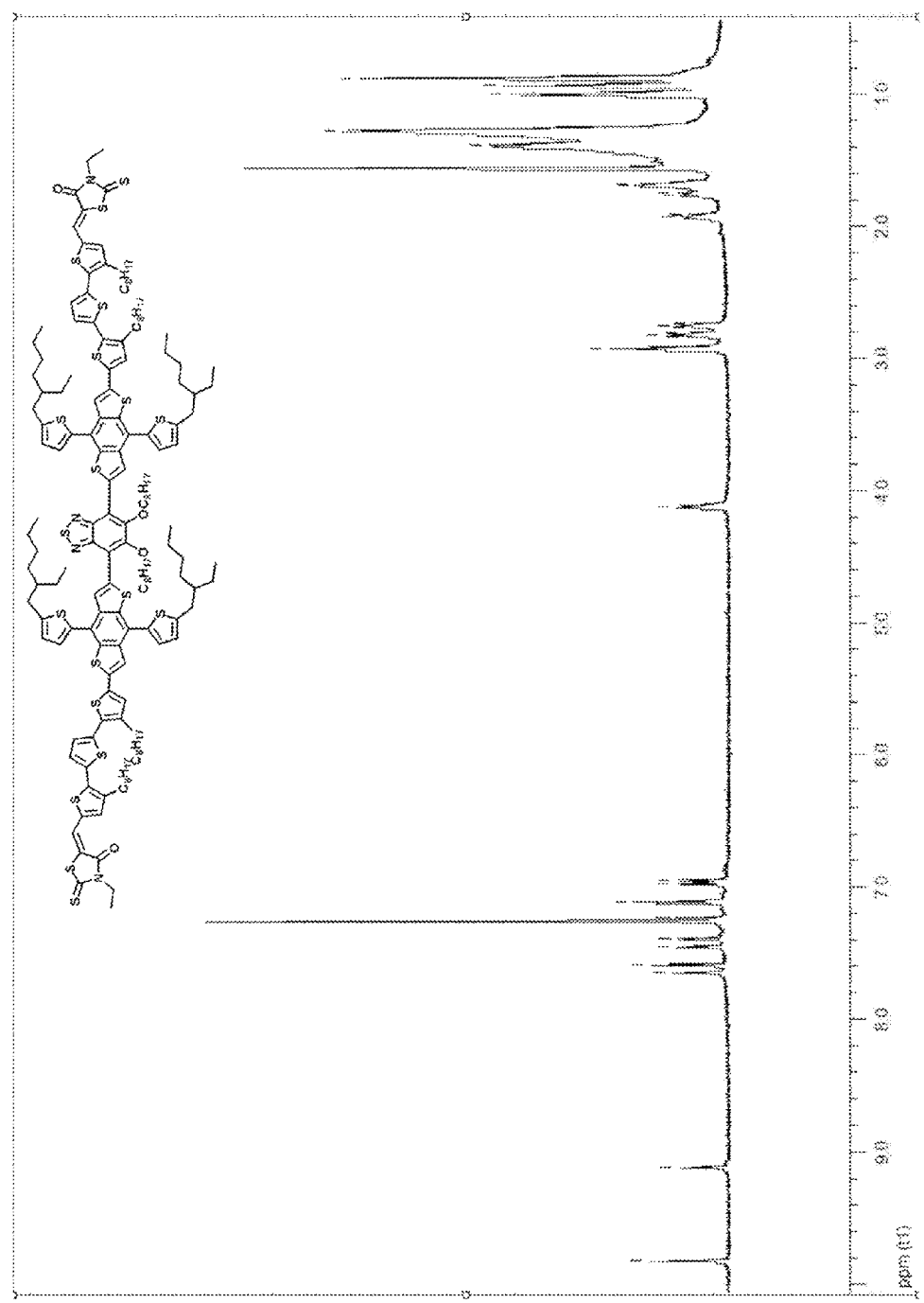

HETEROCYCLIC COMPOUND AND ORGANIC SOLAR CELL COMPRISING SAME

TECHNICAL FIELD

This application is a National Stage Entry of International Application No. PCT/KR2016/001617, filed on Feb. 17, 2016, and claims the benefit of and priority to Korean Application No. 10-2015-0024278, filed on Feb. 17, 2015, all of which are hereby incorporated by reference in their entirety for all purposes as if fully set forth herein.

The present specification relates to a heterocyclic compound and an organic solar cell including the same.

BACKGROUND ART

An organic solar cell is a device that may directly convert solar energy into electric energy by applying a photovoltaic effect. A solar cell may be divided into an inorganic solar cell and an organic solar cell, depending on the materials constituting a thin film. Typical solar cells are made through a p-n junction by doping crystalline silicon (Si), which is an inorganic semiconductor. Electrons and holes generated by absorbing light diffuse to p-n junction points and move to an electrode while being accelerated by the electric field. The power conversion efficiency in this process is defined as the ratio of electric power given to an external circuit and solar power entering the solar cell, and the efficiency have reached approximately 24% when measured under a currently standardized virtual solar irradiation condition. However, since inorganic solar cells in the related art have already shown limitation in economic feasibility and material demands and supplies, an organic semiconductor solar cell, which is easily processed and inexpensive and has various functionalities, has come into the spotlight as a long-term alternative energy source.

For the solar cell, it is important to increase efficiency so as to output as much electric energy as possible from solar energy. In order to increase the efficiency of this solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases, and accordingly, manufacturing costs may be increased.

PATENT DOCUMENT

U.S. Pat. No. 5,331,183
U.S. Pat. No. 5,454,880

DETAILED DESCRIPTION OF THE INVENTION

Technical Problem

An object of the present specification is to provide a heterocyclic compound and an organic solar cell including the same.

Technical Solution

The present specification provides a heterocyclic compound represented by the following Chemical Formula 1.

[Chemical Formula 1]

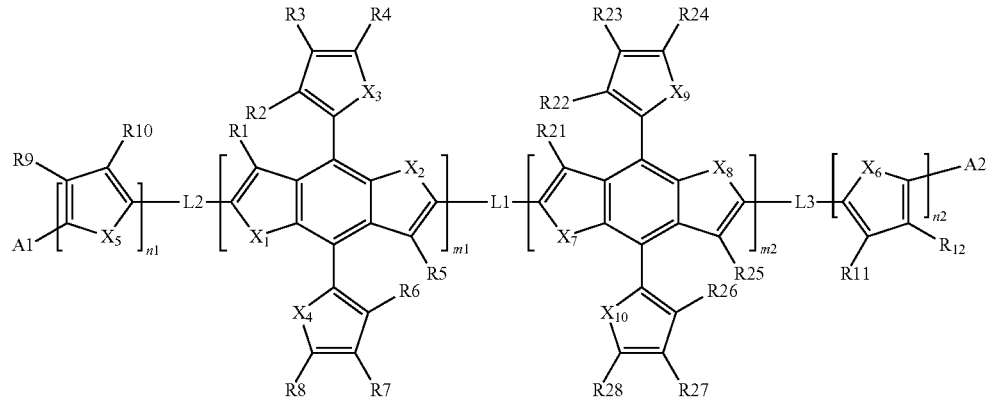

In Chemical Formula 1, m1, m2, n1, and n2 are each an integer from 1 to 3, when m1, m2, n1, and n2 are each 2 or more, two or more structures in the square brackets are the same as or different from each other, L1, L2, and L3 are the same as or different from each other, and are each independently a direct bond; or a divalent linking group, $X_1$ to $X_{10}$ are the same as or different from each other, and are each independently CRR', NR, O, SiRR', PR, S, GeRR', Se, or Te, R, R', R1 to R12, and R21 to R28 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, and S atoms, and A1 and A2 are the same as or different from each other, and are each independently a structure which acts as an electron acceptor.

Further, the present specification provides an organic solar cell including: a first electrode; a second electrode disposed to face the first electrode; and an organic material layer having one or more layers disposed between the first electrode and the second electrode and including a photoactive layer, in which one or more layers of the organic material layer include the above-described heterocyclic compound.

Advantageous Effects

A heterocyclic compound according to an exemplary embodiment of the present specification has a core with a structure including two or more benzodithiophenes (BDTs) having electron donor properties, and thus, has a long effective conjugate length.

Further, the heterocyclic compound according to an exemplary embodiment of the present specification has a core with a structure including two or more benzodithiophenes (BDTs), and thus, may provide a compound having an increased molecular weight.

In addition, the heterocyclic compound according to an exemplary embodiment of the present specification includes L1 which links two benzodithiophenes (BDTs), and thus, has an effect in that the effective conjugate length of the compound becomes relatively long, and the intermolecular interaction may be adjusted by adjusting the substituent of L1 to adjust the torsion angle between L1 and two benzodithiophenes (BDTs).

Accordingly, the heterocyclic compound may be used as a material for an organic material layer of an organic solar cell, and an organic solar cell including the same may exhibit characteristics which are excellent in an increase in open-circuit voltage and short-circuit current, a low band gap effect, and/or an increase in efficiency, and the like.

The heterocyclic compound according to an exemplary embodiment of the present specification may be used either alone or in mixture with other materials in an organic solar cell, and it may be expected to improve the efficiency, and improve the service life of a device by characteristics such as thermal stability of the compound.

BRIEF DESCRIPTION OF DRAWINGS

FIG. 1 is a view illustrating an organic solar cell according to an exemplary embodiment of the present specification.

FIG. 2 is a view illustrating an NMR graph of Compound 1-1.

FIG. 3 is a view illustrating an NMR graph of C which is a starting material in the preparation of Compound 1-2 according to Preparation Example 2.

FIG. 4 is a view illustrating an NMR graph of 1-E which is an intermediate in the preparation of Compound 1-3 according to Preparation Example 3.

FIG. 5 is a view illustrating MS data of Compound 1-13 according to Preparation Example 4.

FIG. 6 is a view illustrating an NMR graph of 1-H which is an intermediate in the preparation of Compound 1-13 according to Preparation Example 4.

BEST MODE

Hereinafter, the present specification will be described in detail.

The present specification provides the heterocyclic compound represented by Chemical Formula 1.

In the present specification,

means a moiety linked to another substituent.

When one part "includes" one constituent element in the present specification, unless otherwise specifically described, this does not mean that another constituent element is excluded, but means that another constituent element may be further included.

Examples of the substituents will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

The term "substituted or unsubstituted" as used herein means being substituted with one or more substituents selected from the group consisting of deuterium; a halogen group; an alkyl group; an alkenyl group; an alkoxy group; an ester group; a carbonyl group; a carboxyl group; a hydroxy group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heterocyclic group; an arylamine group; an aryl group; a nitrile group; a nitro group; a hydroxy group; and a heterocyclic group including one or more of N, O, and S atoms, or having no substituent.

The substituents may be unsubstituted or substituted with an additional substituent.

In the present specification, a halogen group may be fluorine, chlorine, bromine, or iodine.

In the present specification, the number of carbon atoms of an imide group is not particularly limited, but is preferably 1 to 25. Specifically, the imide group may be a compound having the following structures, but is not limited thereto.

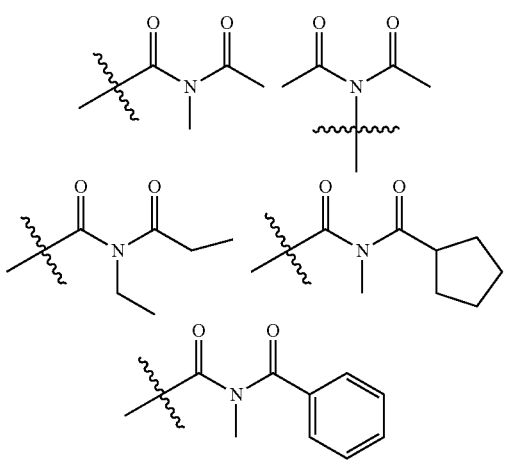

In the present specification, for an amide group, one or two nitrogen atoms of the amide group may be substituted with hydrogen, a straight, branched, or cyclic alkyl group having 1 to 25 carbon atoms, or an aryl group having 6 to 25 carbon atoms. Specifically, the amide group may be a compound having the following structural formulae, but is not limited thereto.

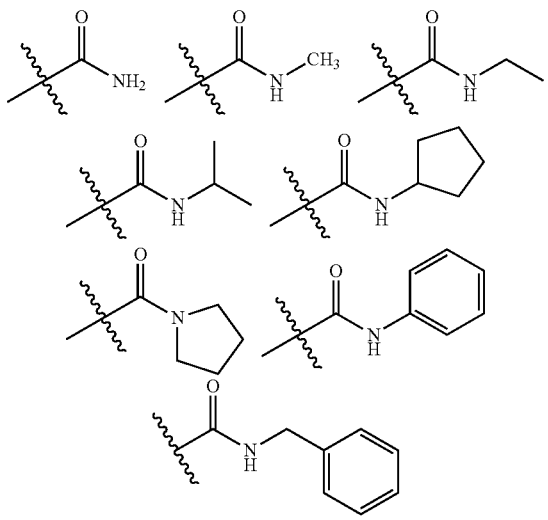

In the present specification, the alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto. In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, the fluorenyl group has a structure in which two cyclic organic compounds are linked to each other through one atom.

In the present specification, the fluorenyl group may be substituted, and adjacent substituents may be bonded to each other to form a ring.

When the fluorenyl group is substituted, the substituent may be

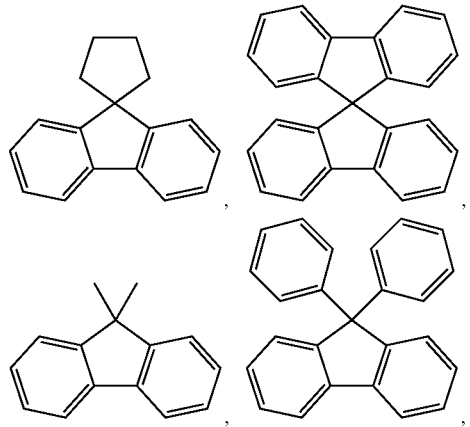

and the like. However, the fluorenyl group is not limited thereto.

In the present specification, the heteroaryl group is a heteroaryl group including one or more of O, N, and S as a hetero element, and the number of carbon atoms thereof is not particularly limited, but is preferably 2 to 60. Examples of the heteroaryl group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a benzothiadiazolyl group, a phenothiazinyl group, a dibenzofuranyl group, and the like, but are not limited thereto.

In the present specification, the heterocyclic group may be monocyclic or polycyclic, may be an aromatic ring, an aliphatic ring, or a fused ring of the aromatic ring and the aliphatic ring, and may be selected from the examples of the heteroaryl group.

In the present specification, examples of an arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the heteroaryl group in the heteroarylamine group may be selected from the above-described examples of the heterocyclic group.

In the present specification, the aryl group in the aryloxy group, the arylthioxy group, the arylsulfoxy group, and the aralkylamine group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, the alkyl group in the alkylthioxy group and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but the examples are not limited thereto.

In the present specification, an arylene group means a group having two bonding positions in an aryl group, that is, a divalent group. The above-described description on the aryl group may be applied to the arylene group, except for a divalent arylene group.

In the present specification, a heteroarylene group means a group having two bonding positions in a heteroaryl group, that is, a divalent group. The above-described description on the heteroaryl group may be applied to the heteroarylene group, except for a divalent heteroarylene group.

According to an exemplary embodiment of the present specification, in Chemical Formula 1, L1 is selected from a direct bond; or the following structures.

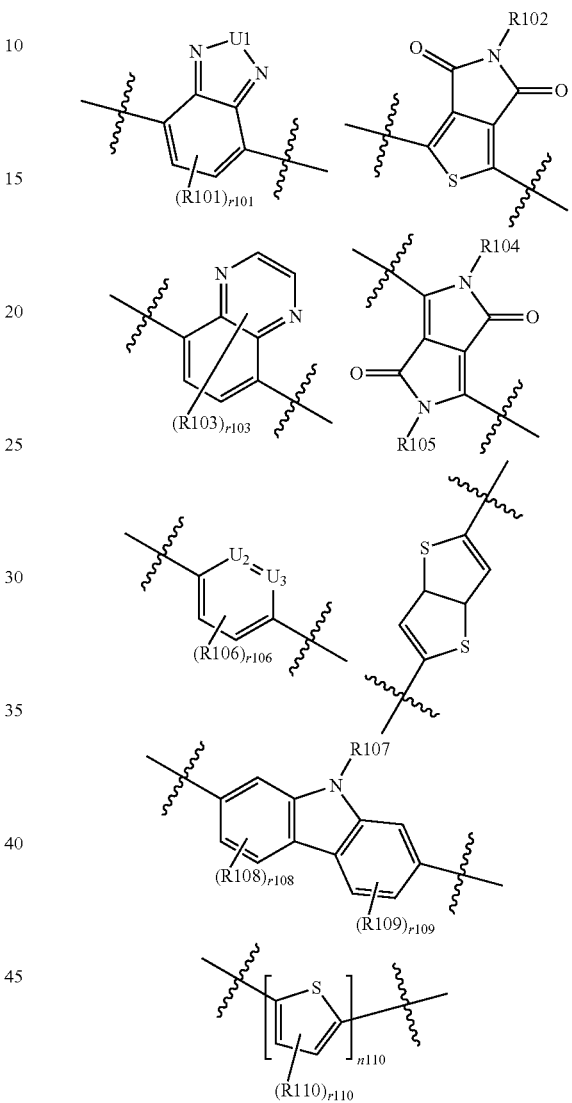

In the structures,

U1 is NR111, S, or O,

U2 and U3 are the same as or different from each other, and are each independently N or CH, R101 to R111 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group;

a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, and S atoms, r101, r106, and r110 are each 1 or 2,
r103 is an integer from 1 to 4,
r108 and r109 are each an integer from 1 to 3,
n110 is an integer of 1 or more, and
when r101, r103, r106, r108, r109, r110, and n110 are each present in a plural number, a plurality of structures in the parenthesis is the same as or different from each other.

According to an exemplary embodiment of the present specification, R101 to R111 are the same as or different from each other, and are each independently hydrogen; a halogen group; a substituted or unsubstituted alkyl group; or a substituted or unsubstituted alkoxy group.

According to an exemplary embodiment of the present specification, R101 to R111 are the same as or different from each other, and are each independently hydrogen; fluorine; or n-octyloxy.

According to an exemplary embodiment of the present specification, in Chemical Formula 1, L1 and L2 are the same as or different from each other, and are each independently a direct bond; or a divalent linking group, and the divalent linking group may include one or more selected from the group consisting of a substituted or unsubstituted alkylene group; a substituted or unsubstituted arylene group; and a substituted or unsubstituted divalent heterocyclic group including one or more of N, O, S, Si, and Ge.

According to an exemplary embodiment of the present specification, in Chemical Formula 1, L1, L2, and L3 are the same as or different from each other, and each independently include one or more selected from the group consisting of a direct bond; a substituted or unsubstituted alkylene group; a substituted or unsubstituted arylene group; and a substituted or unsubstituted divalent heterocyclic group including one or more of N, O, S, Si, and Ge.

According to an exemplary embodiment of the present specification, L1, L2, and L3 are the same as or different from each other, and each independently include one or more selected from the group consisting of a direct bond; and a substituted or unsubstituted divalent heterocyclic group including one or more of N, O, S, Si, and Ge.

According to an exemplary embodiment of the present specification, L1, L2, and L3 are the same as or different from each other, and each independently include one or more selected from the group consisting of a direct bond; a substituted or unsubstituted divalent thiophene group; and a substituted or unsubstituted benzothiadiazolylene group.

According to an exemplary embodiment of the present specification, L1, L2, and L3 are the same as or different from each other, and each independently include one or more selected from the group consisting of a direct bond; a divalent thiophene group; and a benzothiadiazolylene group which is unsubstituted or substituted with an alkoxy group or fluorine.

According to an exemplary embodiment of the present specification, L2 and L3 are a direct bond.

According to an exemplary embodiment of the present specification, L1 includes one or more selected from the group consisting of a direct bond; a divalent thiophene group; and an n-octyloxy group, or a benzothiadiazolylene group which is unsubstituted or substituted with fluorine.

According to an exemplary embodiment of the present specification, L1 is a direct bond.

According to an exemplary embodiment of the present specification, L1 is a divalent thiophene group.

According to an exemplary embodiment of the present specification, L1 is an n-octyloxy group, or a benzothiadiazolylene group which is unsubstituted or substituted with fluorine.

According to an exemplary embodiment of the present specification, in Chemical Formula 1, Ar1 and Ar2 are the same as or different from each other, and are each independently any one of the following structures.

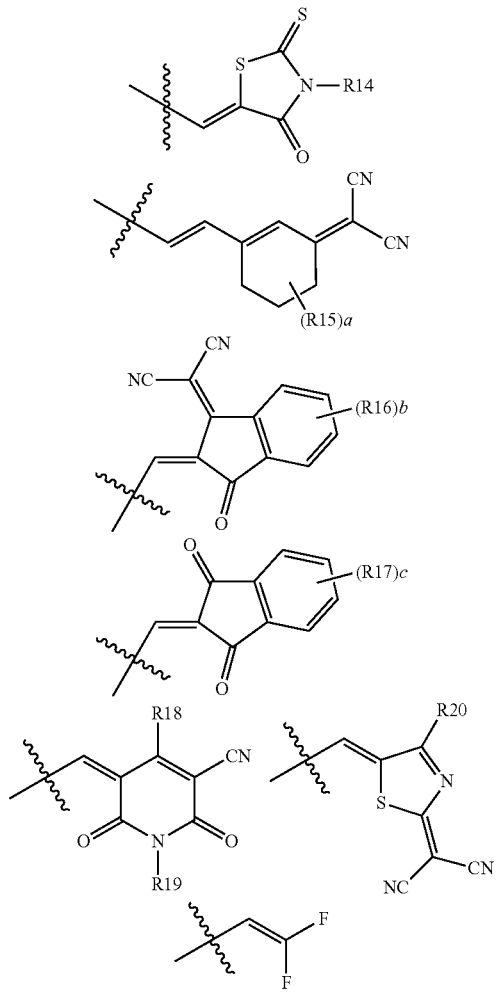

In the structures,
a is an integer from 1 to 7,
b and c are each an integer from 1 to 4,
when a is 2 or more, two or more R15's are the same as or different from each other,
when b is 2 or more, two or more R16's are the same as or different from each other,
when c is 2 or more, two or more R17's are the same as or different from each other, and
R14 to R20 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, and S atoms.

According to an exemplary embodiment of the present specification, in Chemical Formula 1, $X_1$ to $X_{10}$ are S.

According to an exemplary embodiment of the present specification, Chemical Formula 1 may be represented by the following Chemical Formula 1-1.

[Chemical Formula 1-1]

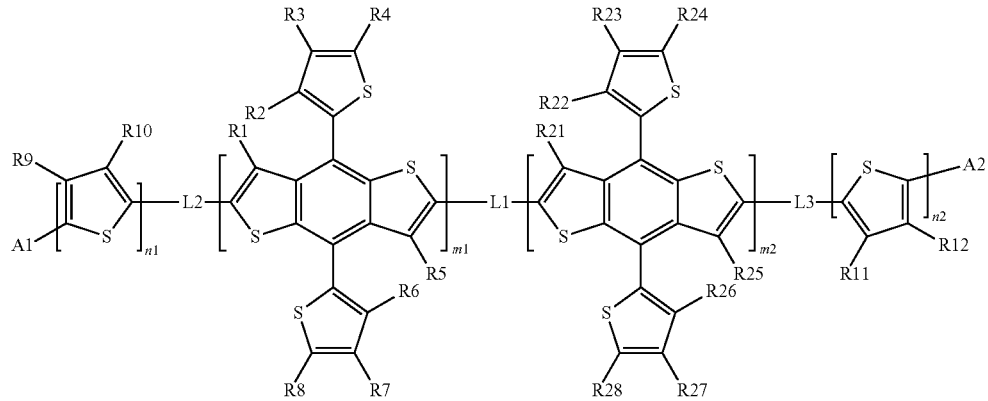

In Chemical Formula 1-1,
the definitions of m1, m2, n1, n2, L1, L2, L3, R1 to R12, R21 to R28, A1, and A2 are the same as those of Chemical Formula 1.

According to an exemplary embodiment of the present specification, Chemical Formula 1 is represented by any one of the following Chemical Formulae 1-2 to 1-10.

[Chemical Formula 1-2]

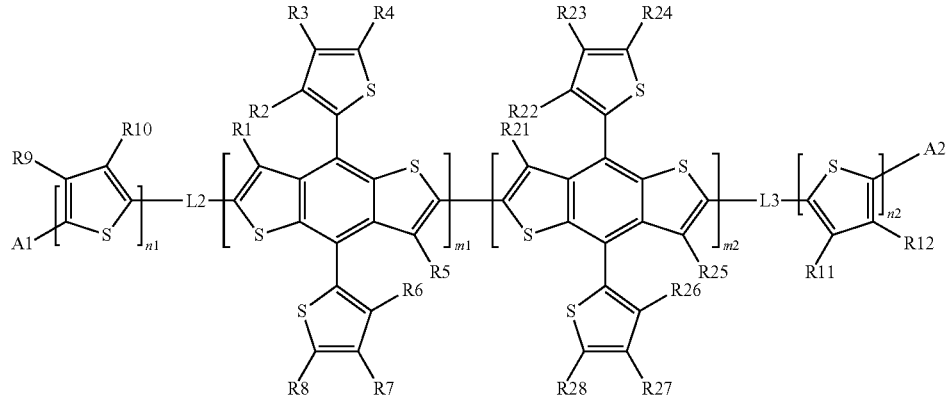

[Chemical Formula 1-3]

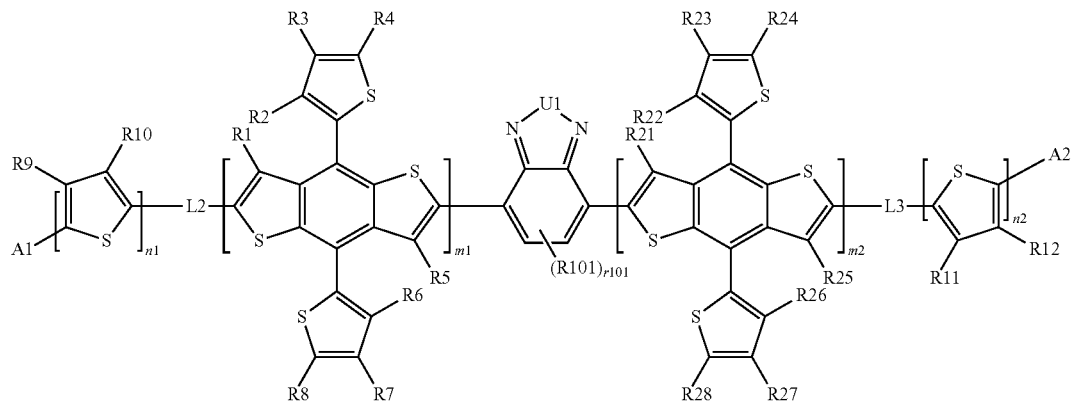

-continued
[Chemical Formula 1-4]
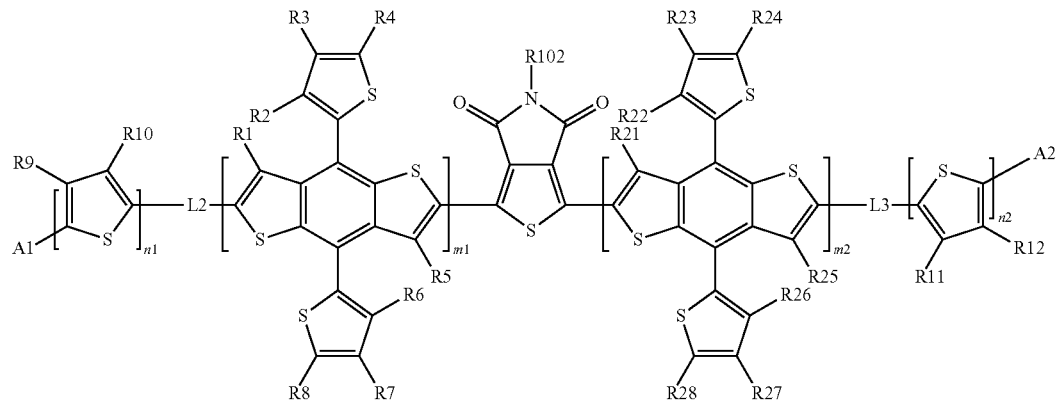
[Chemical Formula 1-5]
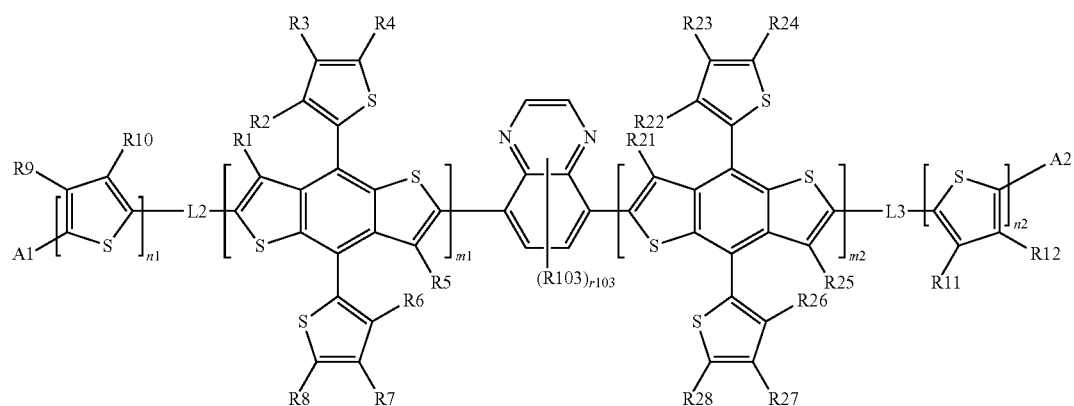
[Chemical Formula 1-6]
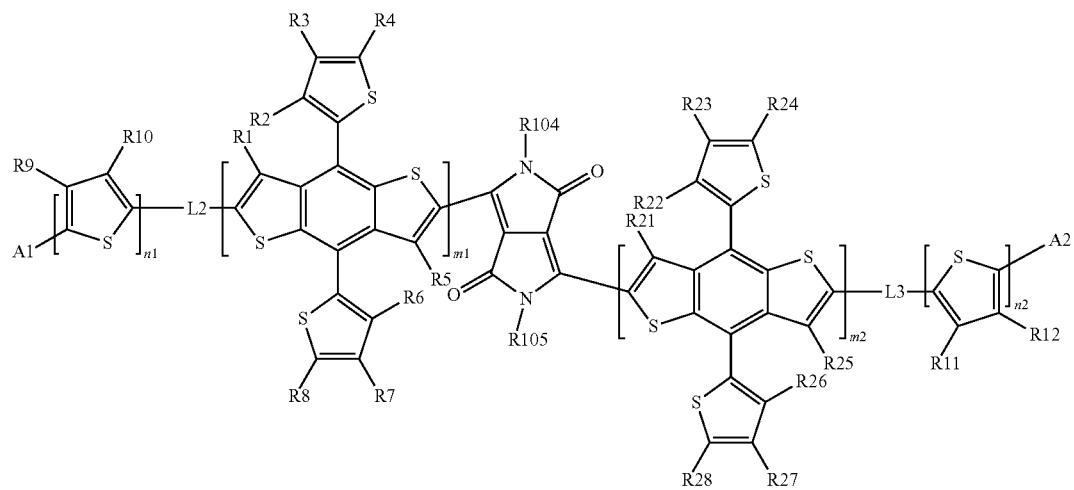

[Chemical Formula 1-7]
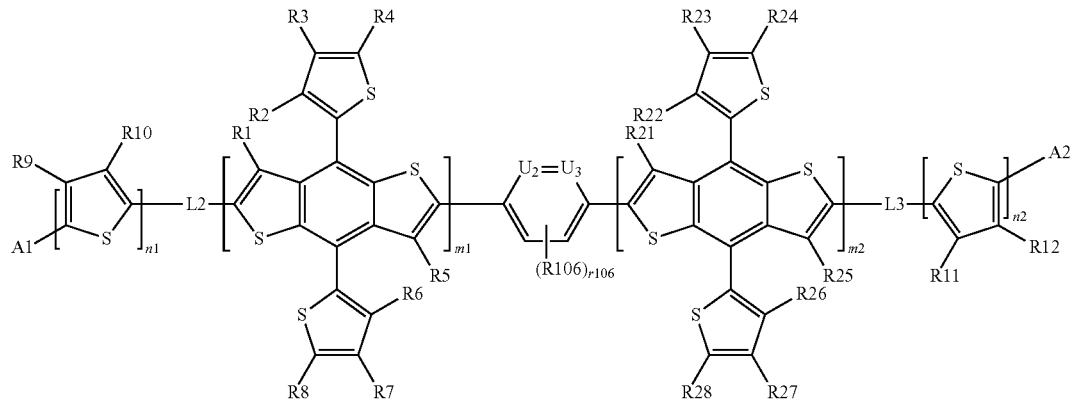
[Chemical Formula 1-8]
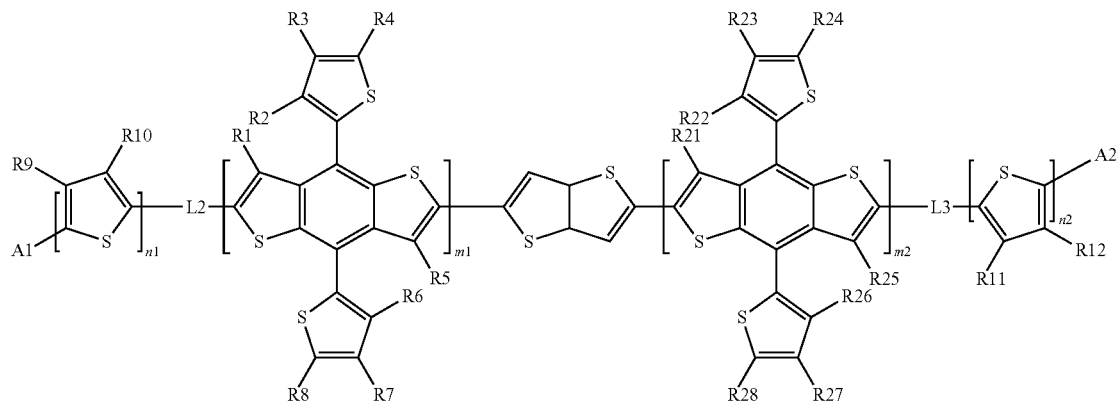
[Chemical Formula 1-9]
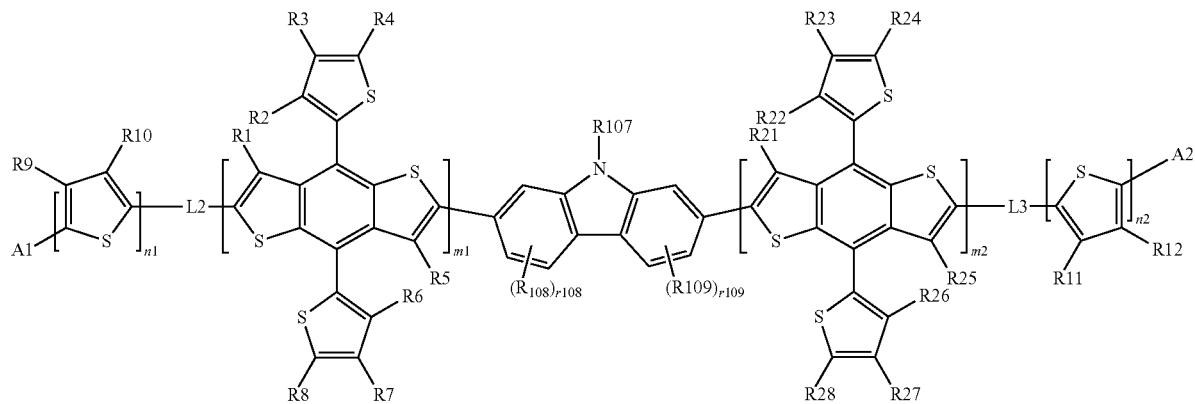

[Chemical Formula 1-10]

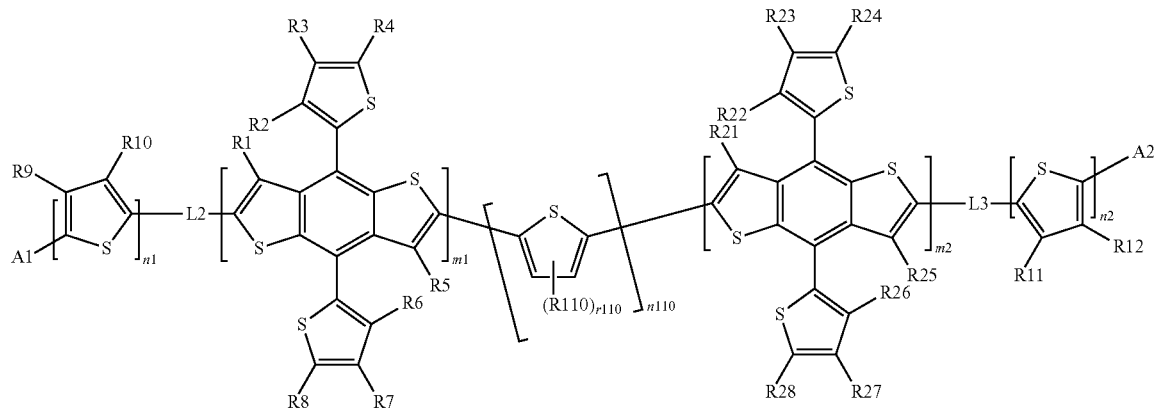

In Chemical Formulae 1-2 to 1-10,
the definitions of m1, m2, n1, n2, L2, L3, R1 to R12, R21 to R28, A1, and A2 are the same as those of Chemical Formula 1, and the definitions of U1 to U3, R101 to R111, r101, r103, r106, r108, r109, r110, and n110 are the same as those described above.

According to an exemplary embodiment of the present specification, in Chemical Formula 1, R1 to R12 and R21 to R28 are the same as or different from each other, and are each independently hydrogen; or a substituted or unsubstituted alkyl group.

According to an exemplary embodiment of the present specification, R1 to R12 and R21 to R28 are the same as or different from each other, and are each independently hydrogen; or a substituted or unsubstituted straight or branched alkyl group having 1 to 30 carbon atoms.

According to an exemplary embodiment of the present specification, R1 to R12 and R21 to R28 are the same as or different from each other, and are each independently hydrogen; or a substituted or unsubstituted straight or branched alkyl group having 1 to 20 carbon atoms.

According to an exemplary embodiment of the present specification, R1 to R12 and R21 to R28 are the same as or different from each other, and are each independently hydrogen; or a substituted or unsubstituted straight or branched alkyl group having 1 to 10 carbon atoms.

According to an exemplary embodiment of the present specification, R1 to R12 and R21 to R28 are the same as or different from each other, and are each independently hydrogen; a substituted or unsubstituted octyl group; or a substituted or unsubstituted 2-ethylhexyl group.

According to an exemplary embodiment of the present specification, R1 to R12 and R21 to R28 are the same as or different from each other, and are each independently hydrogen; an octyl group; or a 2-ethylhexyl group.

According to an exemplary embodiment of the present specification, R4, R8, R24, and R28 are a 2-ethylhexyl group.

According to an exemplary embodiment of the present specification, R9 to R12 are the same as or different from each other, and are each independently hydrogen; or an octyl group.

According to an exemplary embodiment of the present specification, A1 is

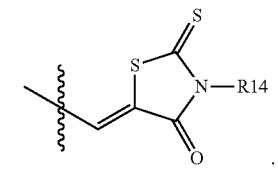

According to an exemplary embodiment of the present specification, A2 is

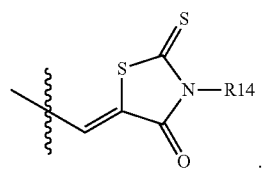

According to an exemplary embodiment of the present specification, R14 is a substituted or unsubstituted alkyl group.

According to an exemplary embodiment of the present specification, R14 is a substituted or unsubstituted straight or branched alkyl group having 1 to 15 carbon atoms.

According to an exemplary embodiment of the present specification, R14 is a substituted or unsubstituted ethyl group.

According to an exemplary embodiment of the present specification, R14 is an ethyl group.

According to an exemplary embodiment of the present specification, m1 is 1.

According to an exemplary embodiment of the present specification, m2 is 1.

According to an exemplary embodiment of the present specification, n1 is 3.

According to an exemplary embodiment of the present specification, n2 is 3.

According to an exemplary embodiment of the present specification, Chemical Formula 1 may be represented by any one of the following Compounds 1-1 to 1-13.

[Compound 1-1]
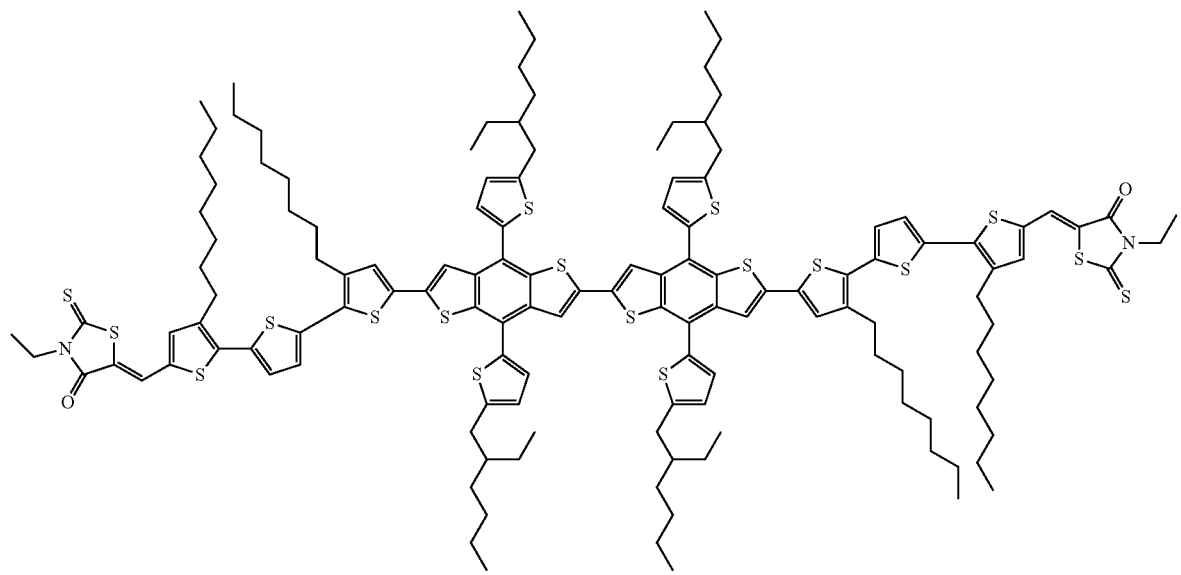
[Compound 1-2]
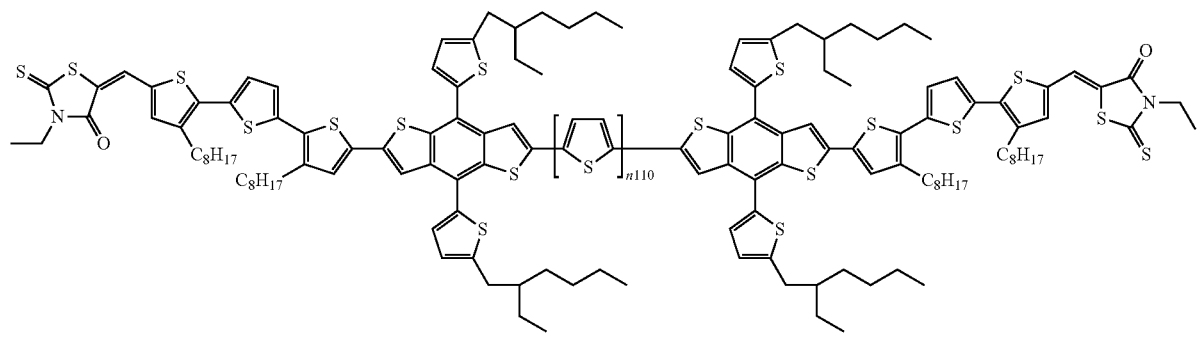
[Compound 1-3]
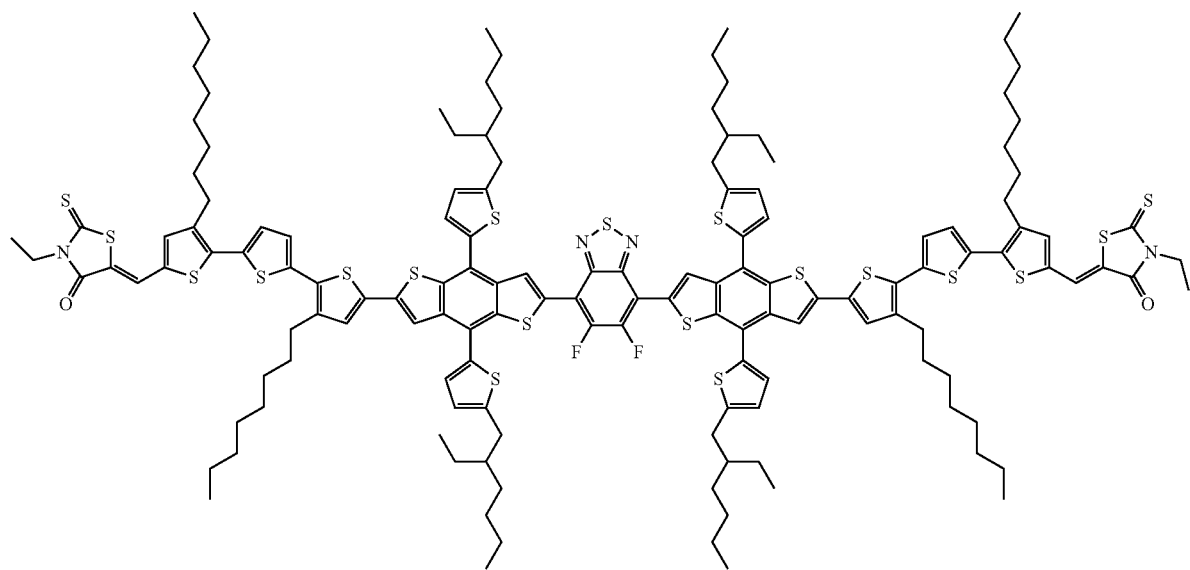

-continued
[Compound 1-4]
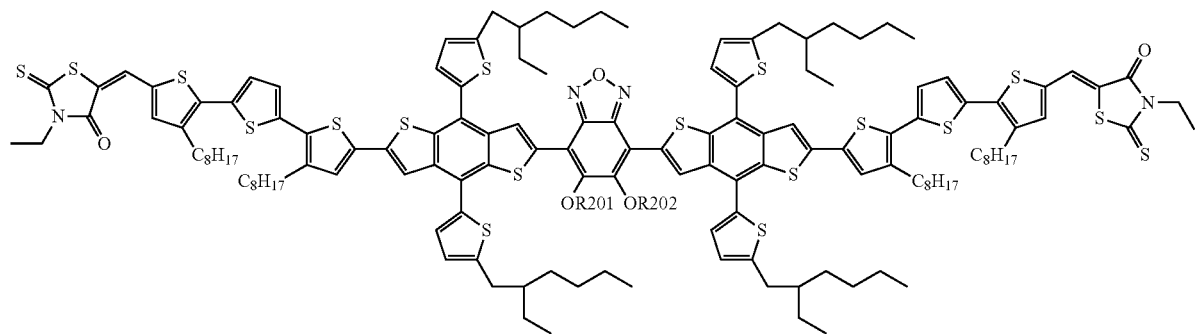
[Compound 1-5]
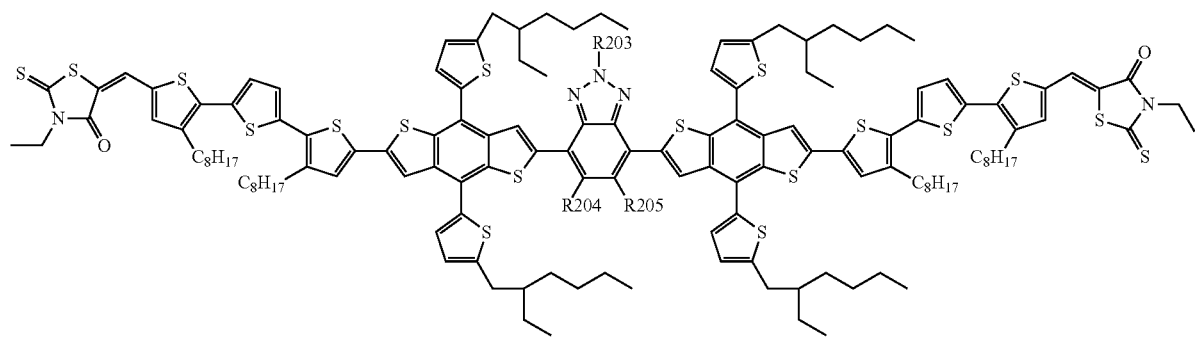
[Compound 1-6]
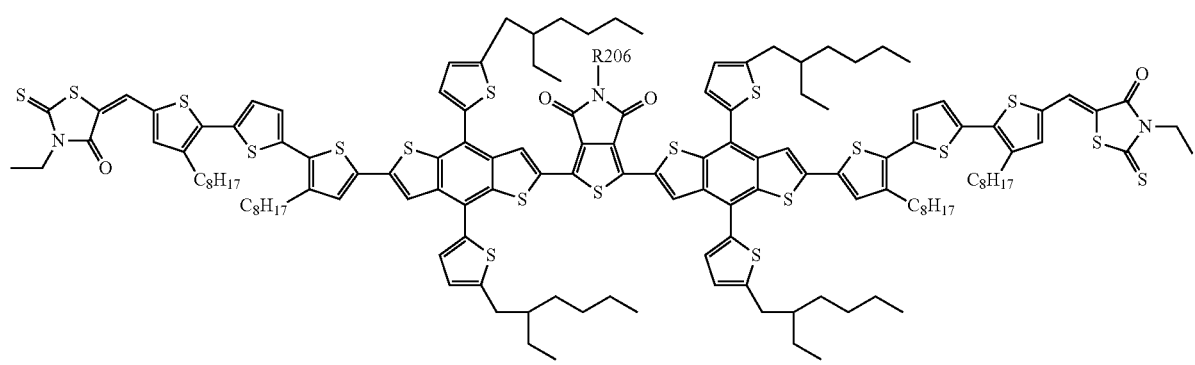
[Compound 1-7]
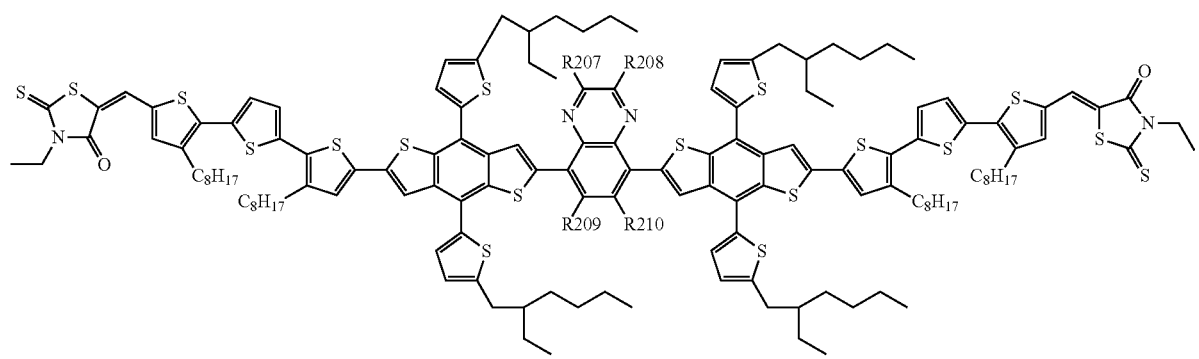

-continued
[Compound 1-8]
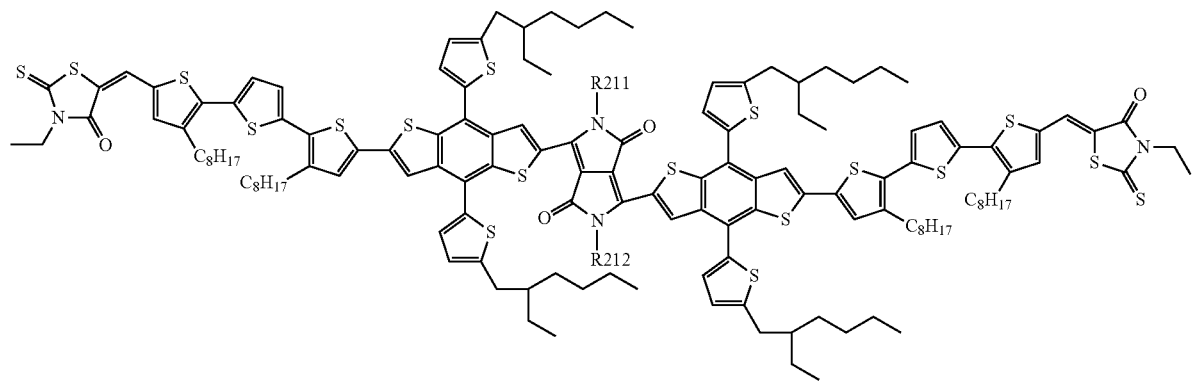
[Compound 1-9]
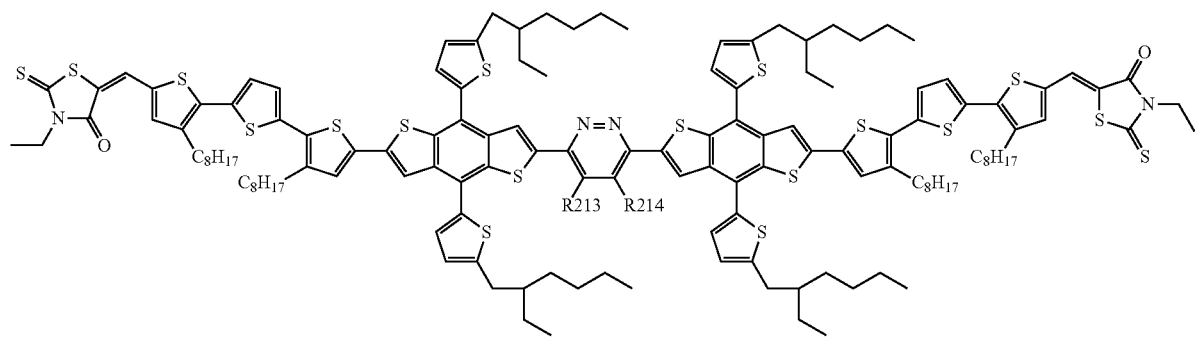
[Compound 1-10]
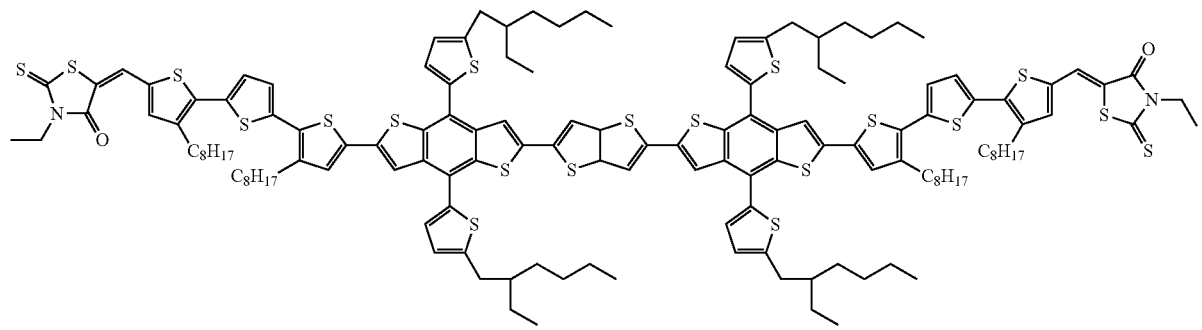
[Compound 1-11]
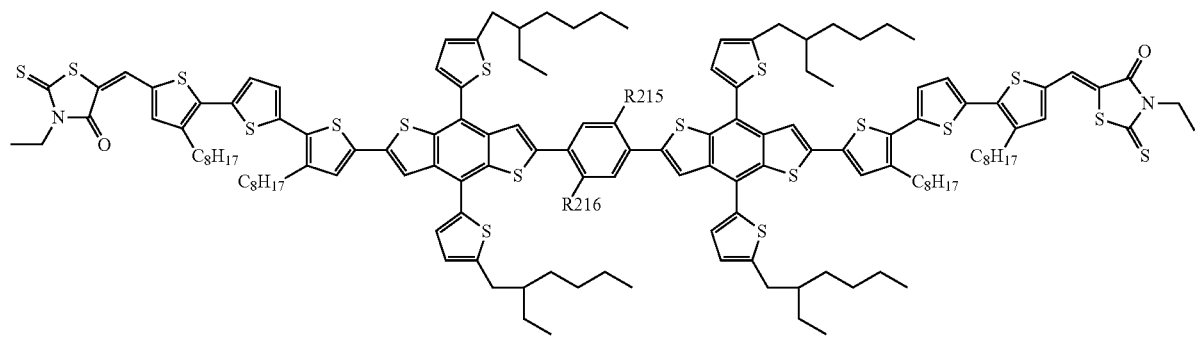

[Compound 1-12]

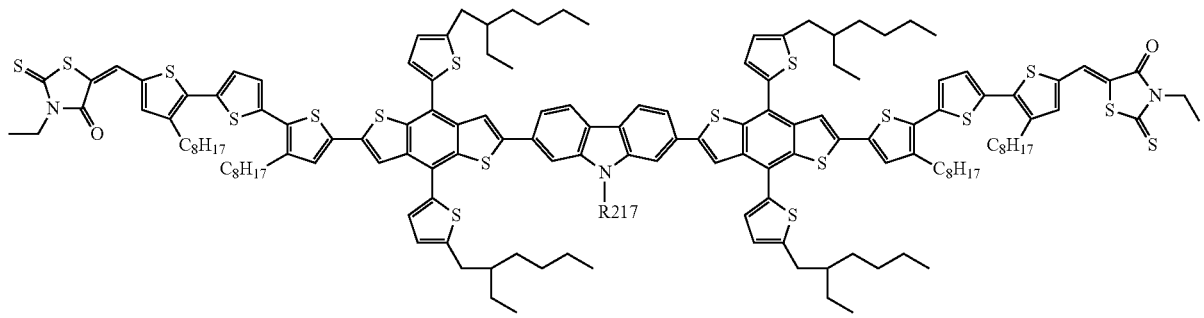

[Compound 1-13]

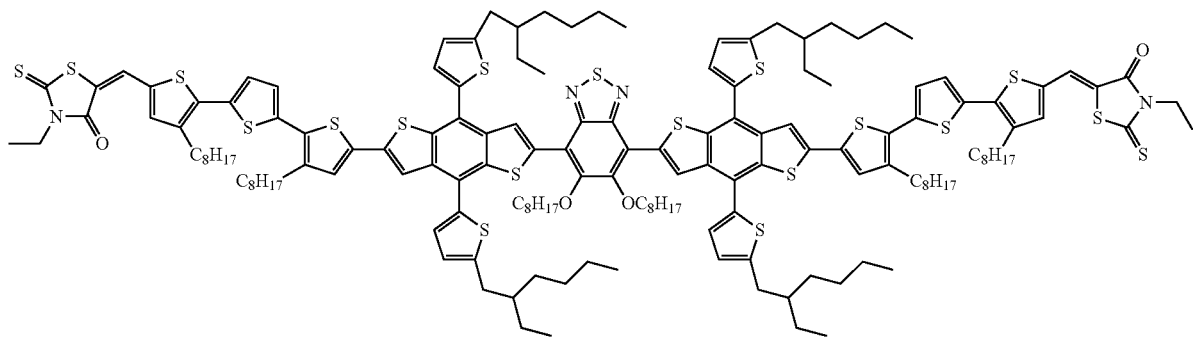

In Compounds 1-2, 1-4 to 1-9, 1-11, and 1-12,
n110 is an integer of 1 or more, and
R201 to R217 are the same as or different from each other, and are each independently hydrogen; deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group including one or more of N, O, and S atoms.

According to an exemplary embodiment of the present specification, in Compounds 1-4 to 1-9, 1-11, and 1-12, R201 to R217 are the same as or different from each other, and are each independently hydrogen; a halogen group; a substituted or unsubstituted alkyl group; or a substituted or unsubstituted alkoxy group.

The heterocyclic compound may be prepared based on the Preparation Examples to be described below.

For the heterocyclic compound according to an exemplary embodiment of the present specification, a structure of m1 in the square bracket is bonded to a structure of m2 in the square bracket through a linking group L1, a compound obtained through the bond is bonded to L2 and L3, and then a compound having a structure obtained through the bond is bonded to a compound having a structure in which aldehyde is introduced into the ends of n1 and n2. Thereafter, by introducing A1 and A2, not only a heterocyclic compound represented by Compound 1-1, but also a heterocyclic compound represented by Chemical Formula 1 may be prepared.

The heterocyclic compound according to an exemplary embodiment of the present specification may be prepared by a multi-step chemical reaction. Monomers are prepared through an alkylation reaction, a Grignard reaction, a Suzuki coupling reaction, a Stille coupling reaction, and the like, and then final heterocyclic compounds may be prepared through a carbon-carbon coupling reaction such as a Stille coupling reaction. When the substituent to be introduced is a boronic acid or boronic ester compound, the final heterocyclic compounds may be prepared through a Suzuki coupling reaction, and when the substituent to be introduced is a tributyltin or trimethyltin compound, the final heterocyclic compounds may be prepared through a Stille coupling reaction, but the method is not limited thereto.

An exemplary embodiment of the present specification provides an organic solar cell including: a first electrode; a second electrode disposed to face the first electrode; and an organic material layer having one or more layers disposed between the first electrode and the second electrode and including a photoactive layer, in which one or more layers of the organic material layer include the heterocyclic compound.

The organic solar cell according to an exemplary embodiment of the present specification includes a first electrode, a photoactive layer, and a second electrode. The organic solar cell may further include a substrate, a hole transporting layer, and/or an electron transporting layer.

According to an exemplary embodiment of the present specification, when the organic solar cell accepts a photon from an external light source, an electron and a hole are generated between an electron donor and an electron acceptor. The generated hole is transported to a positive electrode through an electron donor layer.

According to an exemplary embodiment of the present specification, the organic material layer includes a hole transporting layer, a hole injection layer, or a layer which simultaneously transports and injects holes, and the hole transporting layer, the hole injection layer, or the layer which simultaneously transports and injects holes includes the heterocyclic compound.

In another exemplary embodiment, the organic material layer includes an electron injection layer, an electron transporting layer, or a layer which simultaneously injects and transports electrons, and the electron injection layer, the electron transporting layer, or the layer which simultaneously injects and transports electrons includes the heterocyclic compound.

FIG. 1 is a view illustrating an organic solar cell according to an exemplary embodiment of the present specification.

According to an exemplary embodiment of the present specification, when the organic solar cell accepts a photon from an external light source, an electron and a hole are generated between an electron donor and an electron acceptor. The generated hole is transported to a positive electrode through an electron donor layer.

According to an exemplary embodiment of the present specification, the organic solar cell may further include an additional organic material layer. The organic solar cell may reduce the number of organic material layers by using an organic material which simultaneously has various functions.

According to an exemplary embodiment of the present specification, the first electrode is an anode, and the second electrode is a cathode. In another exemplary embodiment, the first electrode is a cathode, and the second electrode is an anode.

According to an exemplary embodiment of the present specification, in the organic solar cell, a cathode, a photoactive layer, and an anode may be arranged in this order, and an anode, a photoactive layer, and a cathode may be arranged in this order, but the arrangement order is not limited thereto.

In another exemplary embodiment, in the organic solar cell, an anode, a hole transporting layer, a photoactive layer, an electron transporting layer, and a cathode may also be arranged in this order, and a cathode, an electron transporting layer, a photoactive layer, a hole transporting layer, and an anode may also be arranged in this order, but the arrangement order is not limited thereto.

According to an exemplary embodiment of the present specification, the organic solar cell has a normal structure. In the normal structure, a substrate, an anode, an organic material layer including a photoactive layer, and a cathode may be stacked in this order.

According to an exemplary embodiment of the present specification, the organic solar cell has an inverted structure. In the inverted structure, a substrate, a cathode, an organic material layer including a photoactive layer, and an anode may be stacked in this order.

According to an exemplary embodiment of the present specification, the organic solar cell has a tandem structure.

In the organic solar cell according to an exemplary embodiment of the present specification, a photoactive layer may have one layer or two or more layers. The tandem structure may include two or more photoactive layers.

In another exemplary embodiment, a buffer layer may be disposed between the photoactive layer and the hole transporting layer, or between the photoactive layer and the electron transporting layer. In this case, a hole injection layer may be further disposed between an anode and a hole transporting layer. Further, an electron injection layer may be further disposed between a cathode and an electron transporting layer.

According to an exemplary embodiment of the present specification, the photoactive layer includes one or two or more selected from the group consisting of an electron donor and an electron acceptor, and the electron donor material includes the heterocyclic compound.

According to an exemplary embodiment of the present specification, the electron acceptor material may be selected from the group consisting of fullerene, fullerene derivatives, bathocuproine, semi-conducting elements, semi-conducting compounds, and combinations thereof. Specifically, the electron acceptor material is one or two or more compounds selected from the group consisting of fullerene, fullerene derivatives ((6,6)-phenyl-C61-butyric acid-methylester (PCBM) or (6,6)-phenyl-C61-butyric acid-cholesteryl ester (PCBCR)), perylene, polybenzimidazole (PBI), and 3,4,9,10-perylene-tetracarboxylic bis-benzimidazole (PTCBI).

According to an exemplary embodiment of the present specification, the electron donor and the electron acceptor constitute a bulk heterojunction (BHJ).

The bulk heterojunction means that an electron donor material and an electron acceptor material are mixed with each other in a photoactive layer.

According to an exemplary embodiment of the present specification, the photoactive layer has a bilayer thin film structure including an n-type organic material layer and a p-type organic material layer, and the p-type organic material layer includes the heterocyclic compound.

In the present specification, the substrate may be a glass substrate or a transparent plastic substrate having excellent transparency, surface smoothness, ease of handling, and waterproofing properties, but is not limited thereto, and the substrate is not limited as long as the substrate is typically used in the organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples thereof include a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or SnO$_2$:Sb; a conductive polymer such as poly(3-methylthiophene), poly [3,4-(ethylene-1,2-dioxy)thiophene] (PEDOT), polypyrrole, and polyaniline; and the like, but are not limited thereto.

A method of forming the anode electrode is not particularly limited, but the anode electrode may be formed, for example, by being applied onto one surface of a substrate using sputtering, e-beam, thermal deposition, spin coating, screen printing, inkjet printing, doctor blade, or a gravure printing method, or by being coated in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a heating plate at 100 to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer.

Further, during the modification, a polymer thin film may be easily formed on an anode electrode, and the quality of the thin film may also be improved.

Examples of a pre-treatment technology for an anode electrode include a) a surface oxidation method using a parallel flat plate-type discharge, b) a method of oxidizing a surface through ozone produced by using UV (ultraviolet) rays in a vacuum state, c) an oxidation method using oxygen radicals produced by plasma, and the like.

One of the methods may be selected depending on the state of an anode electrode or a substrate. However, even though any method is used, it is preferred to commonly prevent oxygen from leaving from the surface of the anode electrode or the substrate, and maximally suppress moisture and organic materials from remaining. In this case, it is possible to maximize a substantial effect of the pre-treatment.

As a specific example, it is possible to use a method of oxidizing a surface through ozone produced by using UV. In this case, a patterned ITO substrate after being ultrasonically cleaned is baked on a hot plate and dried well, and then introduced into a chamber, and the patterned ITO substrate may be cleaned by ozone generated by reacting an oxygen gas with UV light by operating a UV lamp.

However, the surface modification method of the patterned ITO substrate in the present specification need not be particularly limited, and any method may be used as long as the method is a method of oxidizing a substrate. The cathode electrode may be a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; and a multi-layer structured material such as LiF/Al, LiO$_2$/Al, LiF/Fe, Al:Li, Al:BaF$_2$, and Al:BaF$_2$:Ba, but are not limited thereto.

The cathode electrode may be deposited and formed in a thermal evaporator showing a vacuum degree of $5\times10^{-7}$ torr or less, but the forming method is not limited only to this method.

The hole transporting layer and/or electron transporting layer materials serve to efficiently transfer electrons and holes separated from a photoactive layer to an electrode, and the materials are not particularly limited.

Examples of the hole transporting layer material may be poly(3,4-ethylenediocythiophene) doped with poly(styrene-sulfonic acid (PEDOT:PSS) and molybdenum oxide (MoO$_x$); vanadium oxide (V$_2$O$_5$); nickel oxide (NiO); and tungsten oxide (WO$_x$), and the like, but is not limited thereto.

The electron transporting layer material may be electron-extracting metal oxides, and specific examples thereof include: a metal complex of 8-hydroxyquinoline; a complex including Alq$_3$; a metal complex including Liq; LiF; Ca; titanium oxide (TiO$_x$); zinc oxide (ZnO); and cesium carbonate (Cs$_2$CO$_3$), and the like, but are not limited thereto.

The photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the forming method is not limited thereto.

BEST MODE

A preparation method of the heterocyclic compound and the manufacture of an organic solar cell including the same will be described in detail in the following Preparation Examples and Examples. However, the following Examples are provided for exemplifying the present specification, and the scope of the present specification is not limited thereby.

Preparation Example 1. Preparation of Compound 1-1

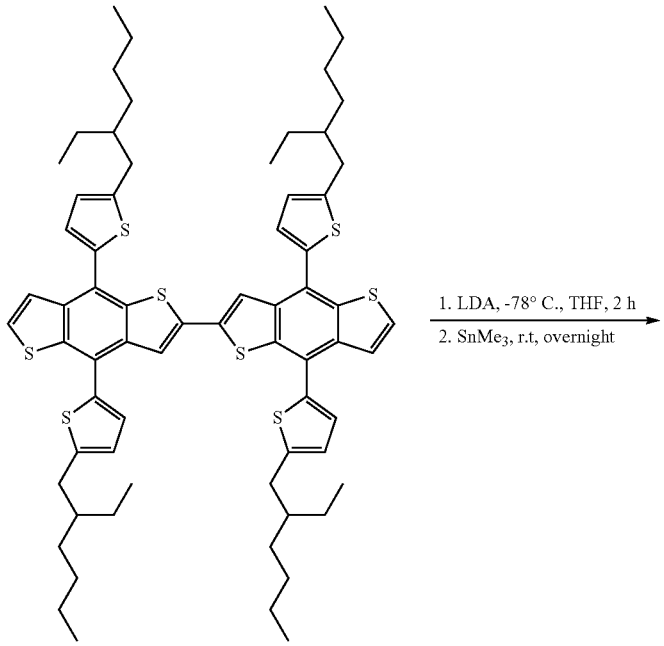

A

-continued
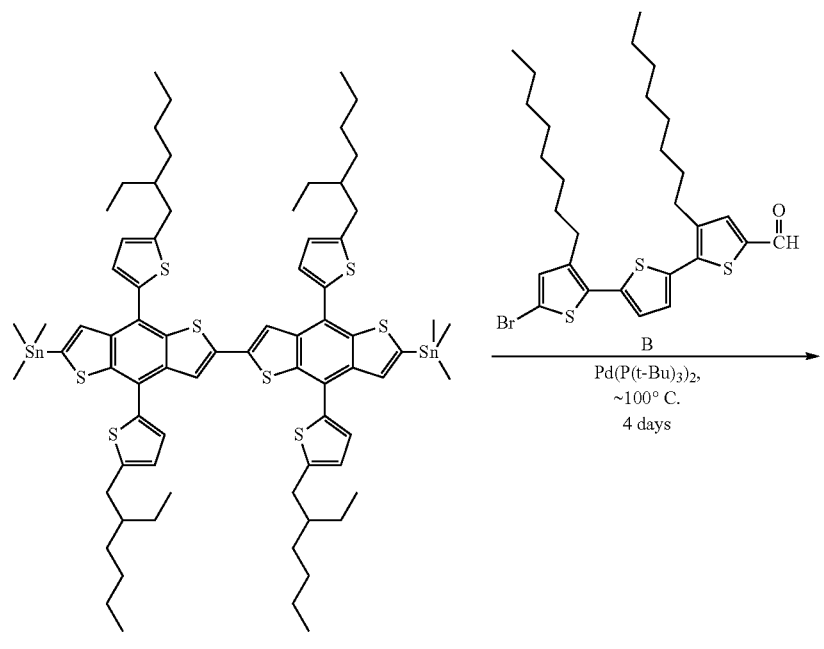
1-A
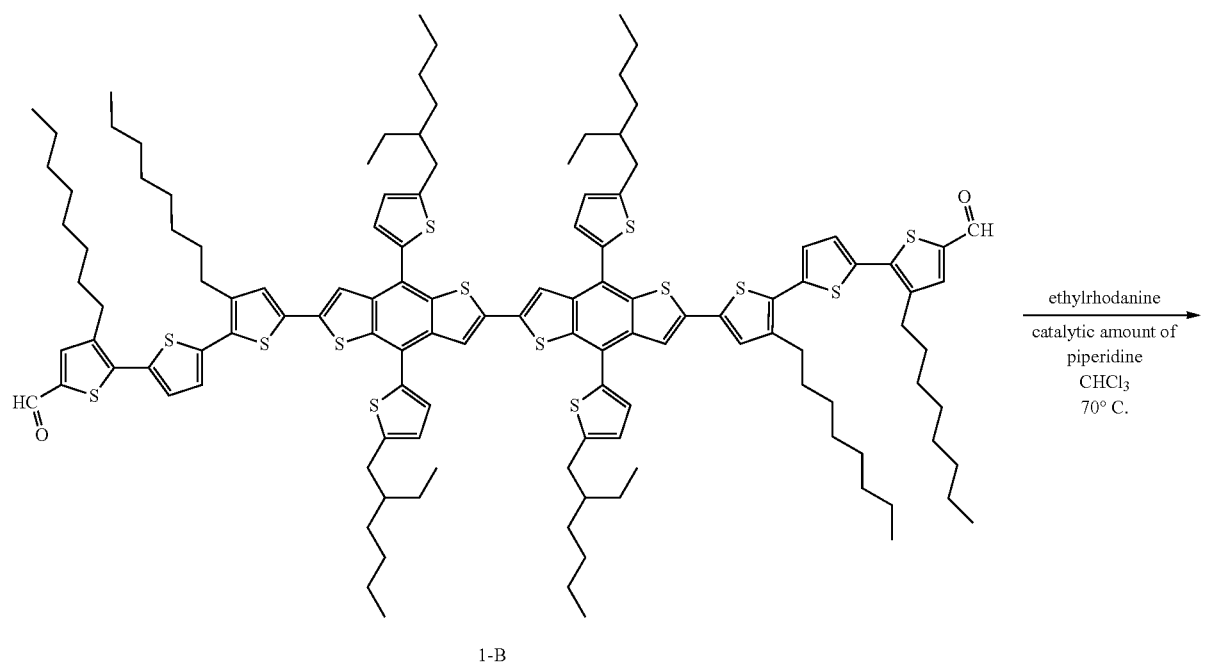
1-B

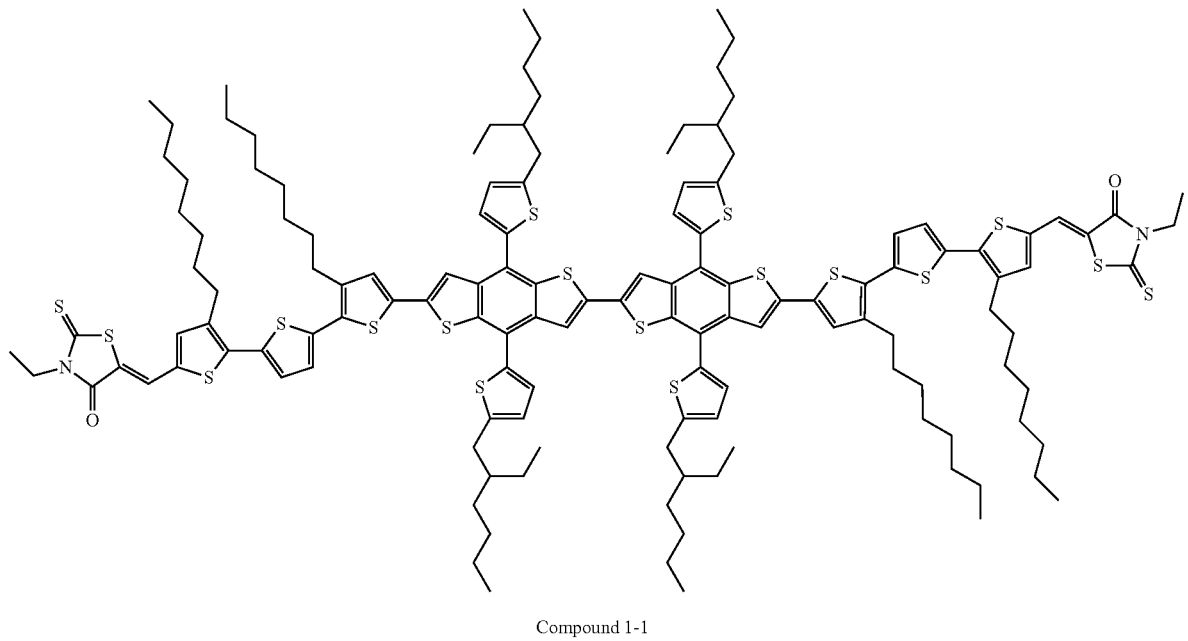

Compound 1-1

Preparation of Compound 1-A 344 mg of A was dissolved in 10 mL of anhydrous tetrahydrofuran, and then the solution was cooled to −78° C. by using a dry ice/acetone bath. A lithium diisopropylamide solution (1.19 mmol, 4.0 equiv.) in 600 mL of 2.0 M tetrahydrofuran (LDA solution in THF) was added to the solution by a drop method. The reaction mixture was stirred at −78° C. for 2 hours, and then a trimethyltin chloride solution (2.7 mmol, 3.0 equiv.) in 1.2 mL of 1.0 M tetrahydrofuran (trimethyltin chloride solution in tetrahydrofuran) was added thereto at the same temperature. The dry ice bath was removed, and then the reaction mixture was stirred for 12 hours. The reaction mixture was poured into 10 mL of iced water, and then extracted three times by using ethyl acetate. An organic layer obtained by collecting the extract was dried by using magnesium sulfate, and then the solvent was completely removed by using reduced pressure. A yellow oil thus obtained was spontaneously crystallized at room temperature, and the resulting crystals were washed with methanol, thereby obtaining Compound 1-A in the form of a yellow powder (405 mg, yield=91%)

Preparation of Compound 1-B

The mass of 7 mg of bis-(tri-t-butylphosphine)palladium (0.014 mmol, 0.05 equiv.) was measured by a reaction dish in a glove box. A solution in which 405 mg of Compound 1-A (0.27 mmol, 1.0 equiv.) and 664 mg of Compound B (1.15 mmol, 4.2 equiv.) were dissolved in toluene from which 9 mL of gas had been removed was injected into the mixture. The reaction mixture thus obtained was stirred at 90° C. for 3 days. The reaction mixture was cooled to room temperature, and then the reaction was terminated by injecting 10 mL of iced water into the mixture, and the mixture was extracted three times with dichloromethane. An organic layer obtained by collecting the extract was dried over magnesium sulfate, and the solvent was removed by reducing pressure. A red oil thus obtained was purified by using a silica column (eluent: chloroform), thereby obtaining Compound 1-B in the form of a blackish red solid. (170 mg, yield=31%)

Preparation of Compound 1-1

188 mg of Compound 1-B (0.087 mmol, 1.0 equiv.) and 140 mg of 3-ethylrhodanine (0.87 mmol, 10 equiv.) were dissolved in 5 mL of anhydrous chloroform, and then a catalytic amount of piperidine was added thereto. The reaction mixture thus obtained was stirred at 70° C. for 12 hours. The reaction mixture was cooled to room temperature, and then was subjected to silica gel chromatography with chloroform, thereby obtaining Compound 1-1. (130 mg, yield=60%)

Preparation Example 2. Preparation of Compound 1-2
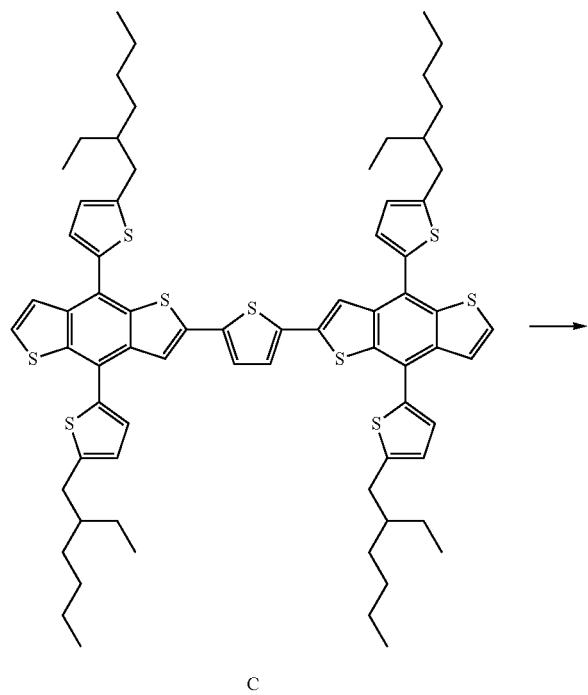
C
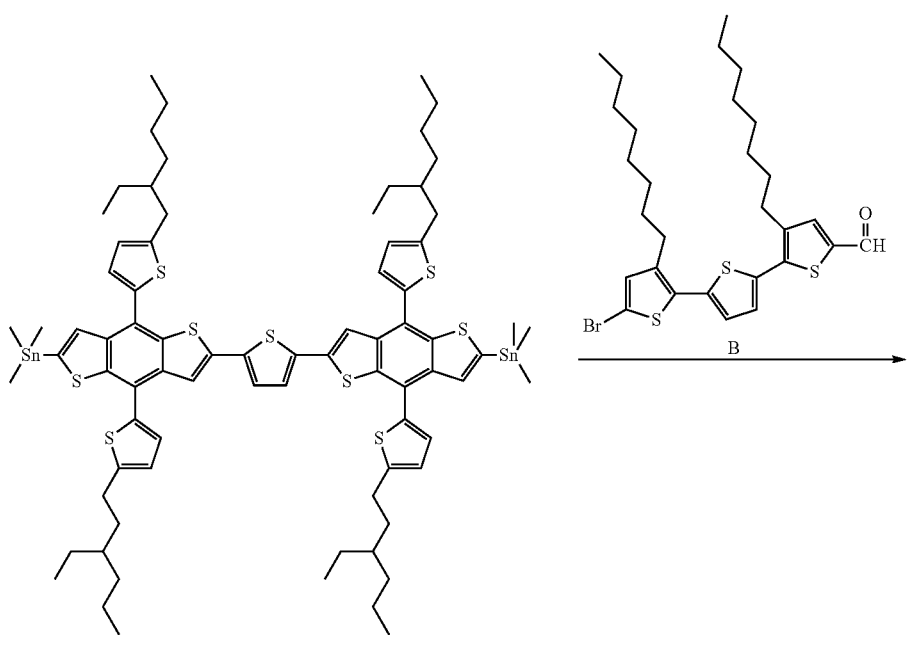

-continued
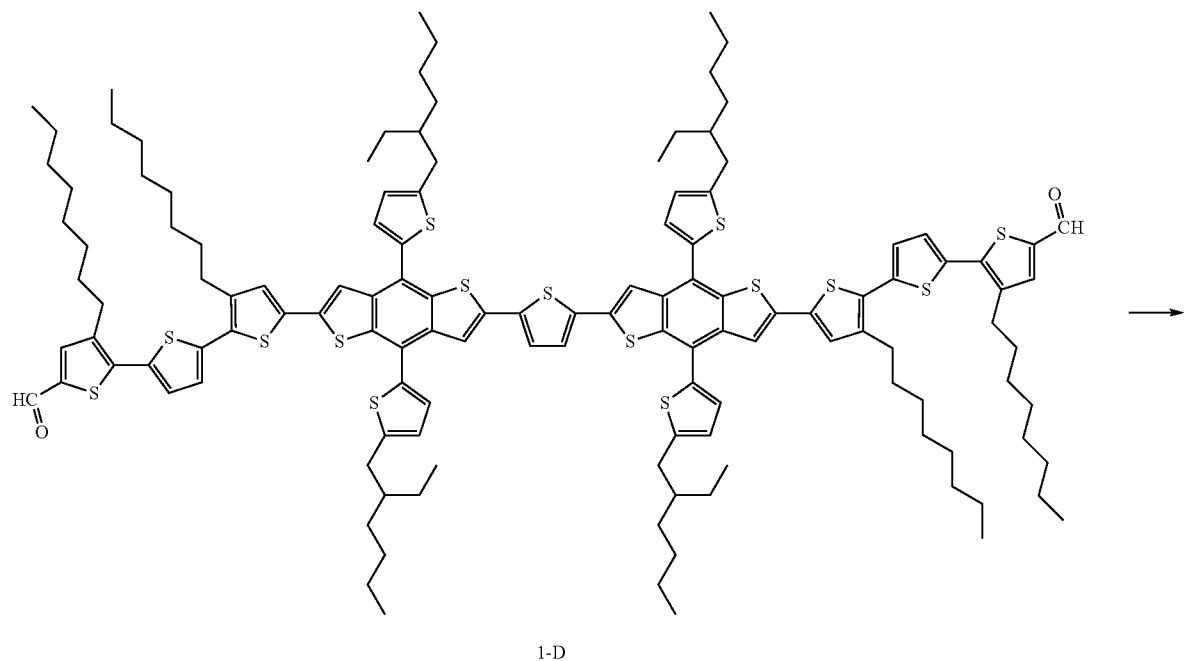
1-D
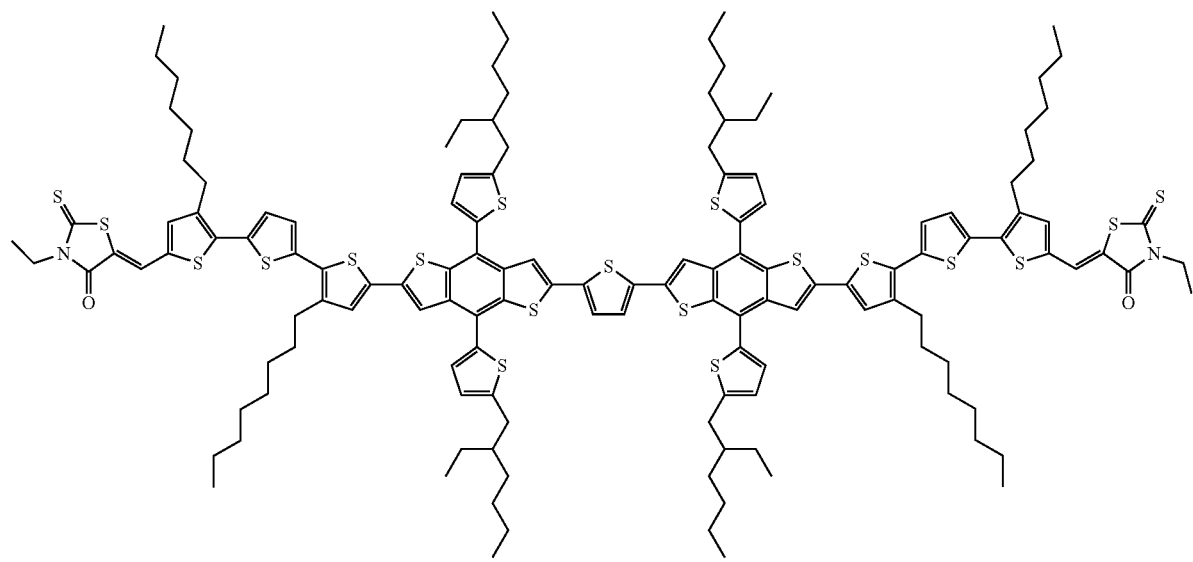
Compound 1-2
Compound 1-2 was prepared in the same manner as in Preparation Example 1, except that Compound C was used instead of Compound A in Preparation Example 1.

Preparation Example 3. Preparation of Compound 1-3
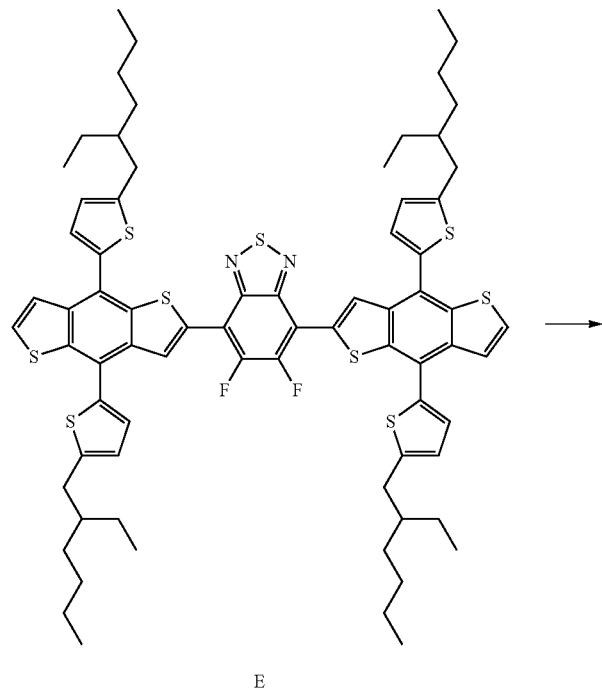
E
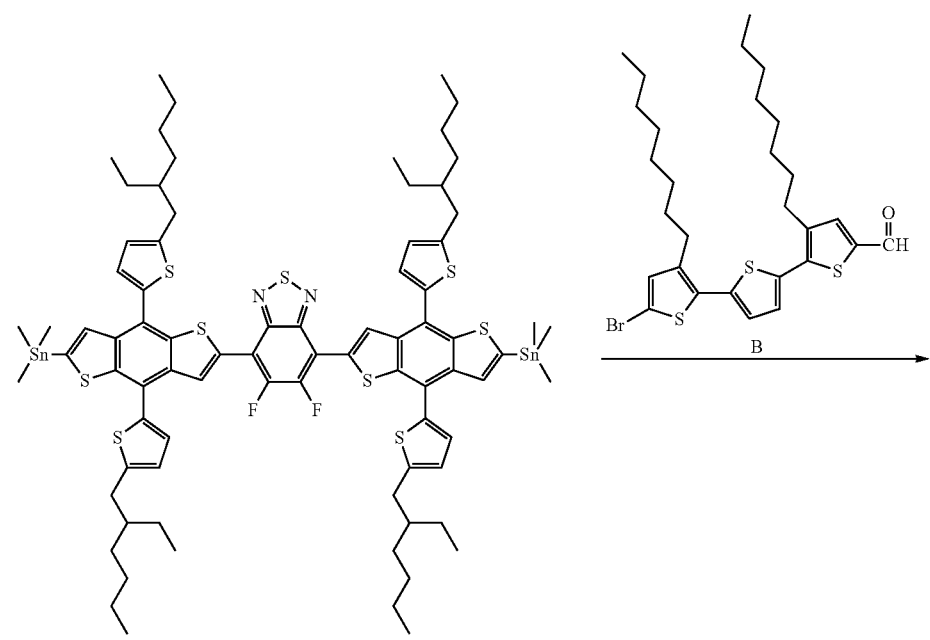

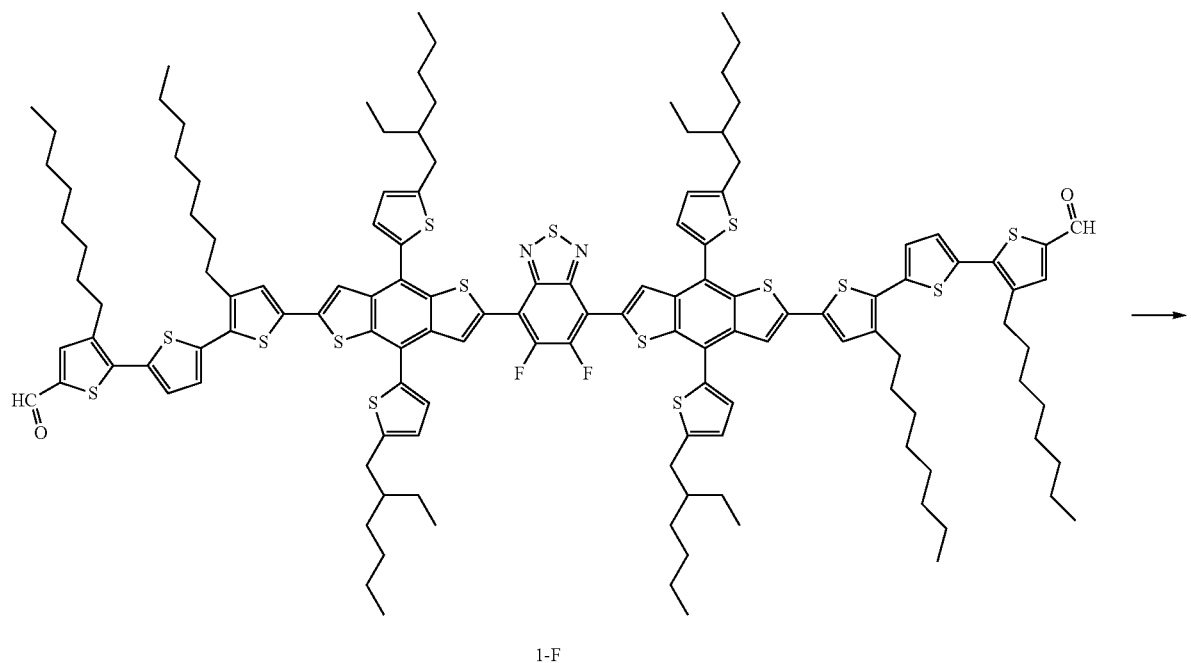
1-F
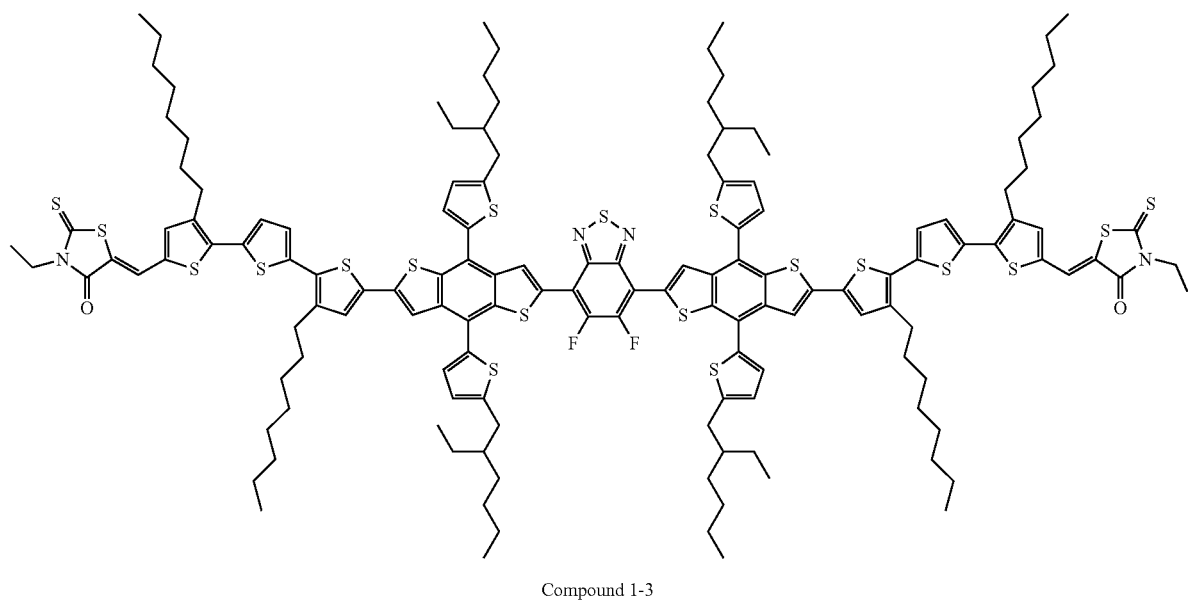
Compound 1-3
Compound 1-3 was prepared in the same manner as in Preparation Example 1, except that Compound E was used instead of Compound A in Preparation Example 1.

Preparation Example 4. Preparation of Compound 1-13
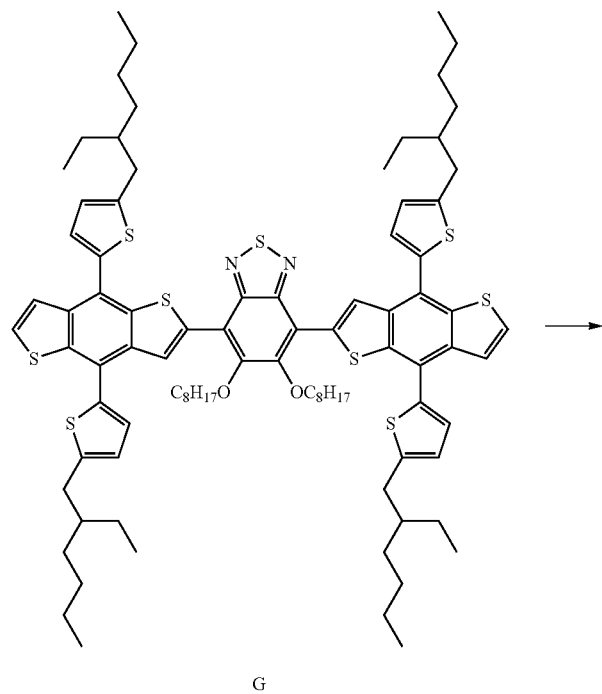
G
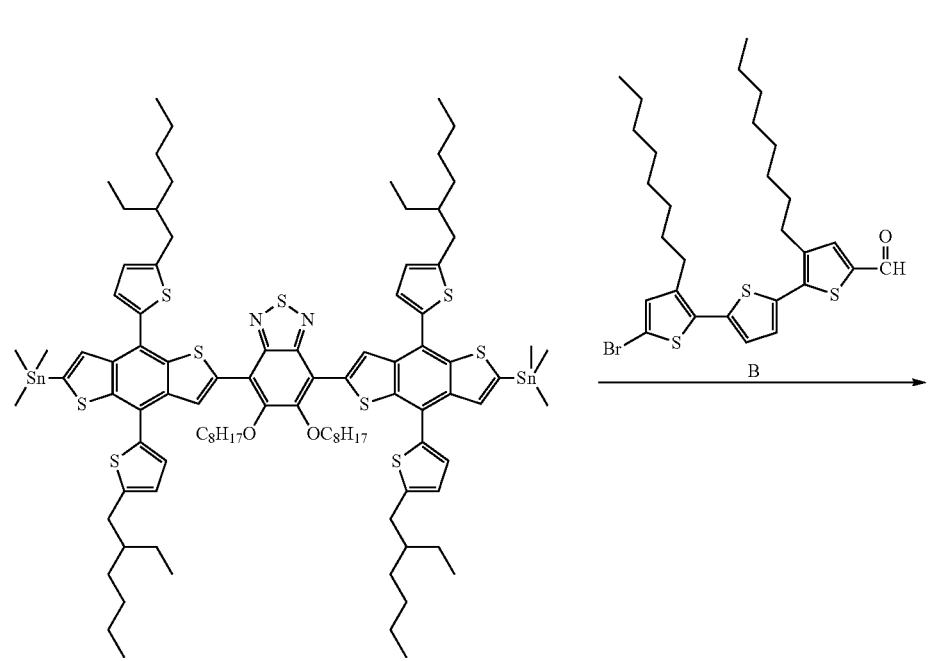
1-G

-continued

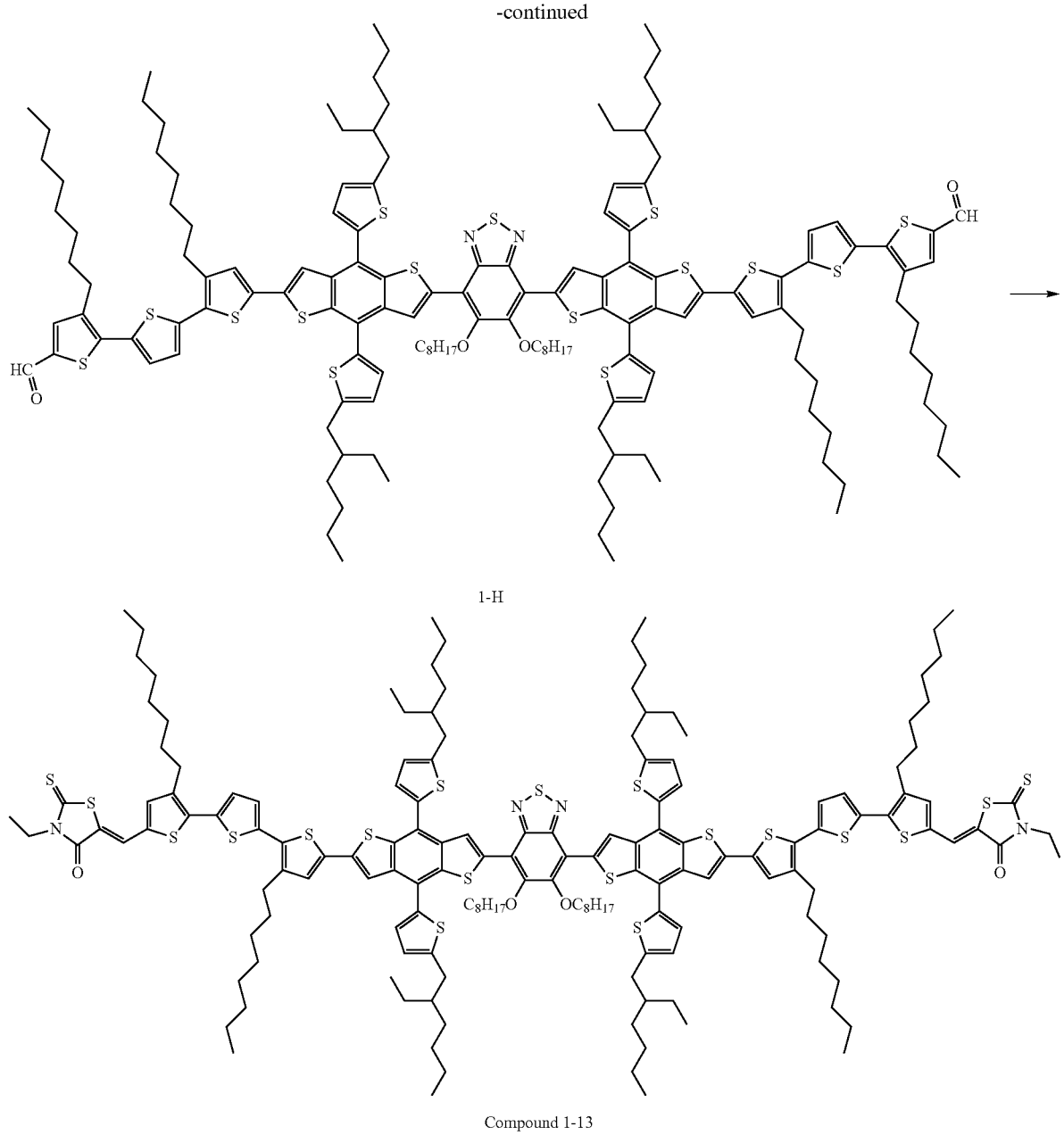

Compound 1-13

Compound 1-13 was prepared in the same manner as in Preparation Example 1, except that Compound G was used instead of Compound A in Preparation Example 1, and the MS data of Compound 1-13 are shown in FIG. 5.

Example 1. Manufacture of Organic Solar Cell

A composite solution was prepared by dissolving Compound 1-13 prepared in Preparation Example 4 and $PC_{71}BM$ at a ratio of 1:1 in chloroform (CF). In this case, the concentration was adjusted to 1.5 wt %, and the organic solar cell was made to have a structure of $ITO/MoO_3/a$ photoactive layer/Al. A glass substrate coated with ITO was ultrasonically cleaned by using distilled water, acetone, and 2-propanol, the ITO surface was treated with ozone for 15 minutes, and then $MoO_3$ was vacuum deposited thereon to have a thickness of 9 nm ($1.1 \times 10^{-7}$ torr). In order to coat the photoactive layer, LiF was deposited to have a thickness of 7 Å under a vacuum of $8.5 \times 10^{-8}$ torr by spin-coating the composite solution of Compound 1-13 and $PC_{71}BM$ at 800 to 200 rpm, and then Al was deposited to have a thickness of 100 nm by using a thermal evaporator under a vacuum of $3 \times 10^{-8}$ torr, thereby manufacturing an organic solar cell.

Evaluation Example 1

The photoelectric conversion characteristics of the organic solar cell manufactured in Preparation Example 1 were measured under the condition of 100 mW/cm² (AM 1.5), and the results are shown in the following Table 1.

TABLE 1

| | $V_{OC}$ (V) | $J_{SC}$ (mA/cm$^2$) | FF (%) | PCE (%) | PCE$_{avg}$ (%) |
|---|---|---|---|---|---|
| Example 1 | 0.860 | 12.320 | 0.552 | 5.85 | 5.74 ± 0.11 |
| | 0.863 | 12.021 | 0.543 | 5.63 | |
| | 0.874 | 12.011 | 0.491 | 5.15 | 5.44 ± 0.28 |
| | 0.853 | 12.171 | 0.551 | 5.72 | |
| | 0.853 | 12.427 | 0.565 | 5.99 | 5.85 ± 0.10 |
| | 0.859 | 12.187 | 0.550 | 5.76 | |
| | 0.860 | 12.079 | 0.559 | 5.81 | |

According to Table 1, it can be confirmed that the organic solar cell manufactured by using the heterocyclic compound according to an exemplary embodiment of the present specification exhibits high efficiency.

Examples 2 to 4 Manufacture of Organic Solar Cell

The organic solar cell manufactured in Example 1 was thermally treated at 60, 80, or 100° C.

Evaluation Example 2

The photoelectric conversion characteristics of the organic solar cells manufactured in Preparation Examples 2 to 4 were measured under the condition of 100 mW/cm$^2$ (AM 1.5), and the results are shown in the following Table 2.

TABLE 2

| | Heat treatment temperature (° C.) | $V_{OC}$ (V) | $J_{SC}$ (mA/cm$^2$) | FF (%) | PCE (%) | PCE$_{avg}$ (%) |
|---|---|---|---|---|---|---|
| Example 2 | 60 | 0.890 | 12.877 | 0.562 | 6.43 | 6.09 ± 0.25 |
| | | 0.889 | 12.539 | 0.539 | 6.01 | |
| | | 0.888 | 12.286 | 0.536 | 5.84 | |
| Example 3 | 80 | 0.885 | 13.543 | 0.578 | 6.93 | 6.73 ± 0.15 |
| | | 0.874 | 13.406 | 0.572 | 6.70 | |
| | | 0.873 | 13.207 | 0.569 | 6.56 | |
| Example 4 | 100 | 0.882 | 13.059 | 0.642 | 7.39 | 7.21 ± 0.13 |
| | | 0.876 | 12.857 | 0.636 | 7.16 | |
| | | 0.876 | 12.736 | 0.634 | 7.08 | |

According to Table 2, when the organic solar cell manufactured by using the heterocyclic compound according to an exemplary embodiment of the present specification is thermally treated, the S-shaped curve shown after the open voltage is applied disappears, and an aspect in which the efficiency is increased is observed because the current density and the fill factor are significantly increased is observed. The aspect means that the charge collection capability may be improved by adjusting the morphology of the photoactive layer, adhesion properties of the photoactive layer with the interface, and the energy barrier by means of the heat treatment, and accordingly, it can be seen that the organic solar cell according to an exemplary embodiment of the present specification has excellent thermal stability and process convenience.

$V_{oc}$, $J_{sc}$, FF, and PCE(η) mean an open-circuit voltage, a short-circuit current, a fill factor, and energy conversion efficiency, respectively. The open-circuit voltage and the short-circuit current are an X axis intercept and an Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred.

EXPLANATION OF REFERENCE NUMERALS AND SYMBOLS

101: Substrate
102: First electrode
103: Hole transporting layer
104: Photoactive layer
105: Second electrode

The invention claimed is:

1. A heterocyclic compound of any one of Compounds 1-3 to 1-9 or 1-13:

[Compound 1-3]

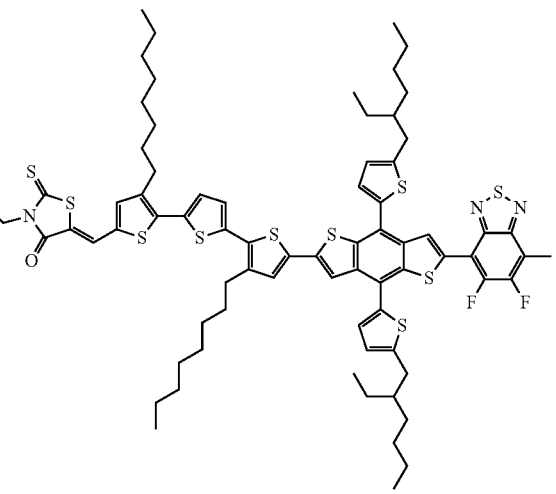

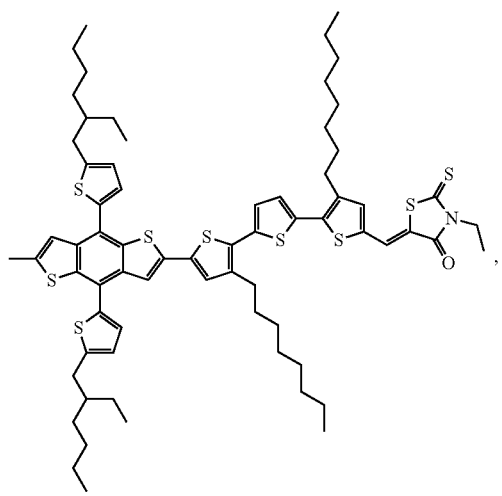

[Compound 1-4]
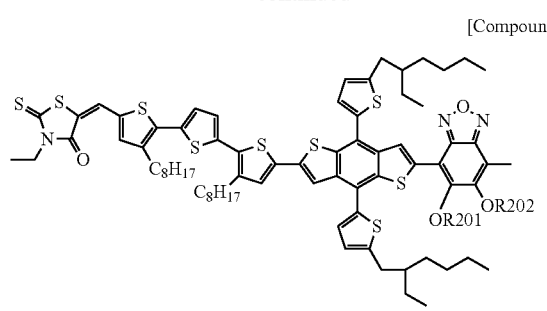
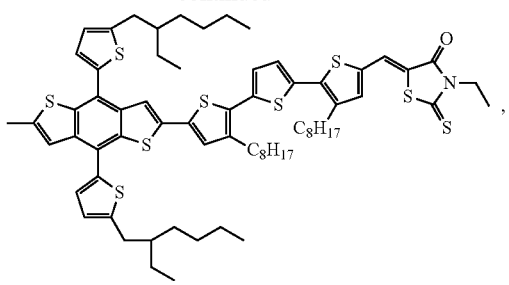
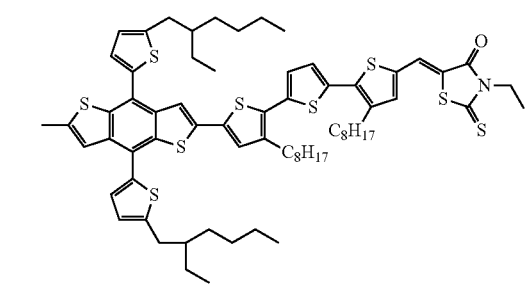
[Compound 1-7]
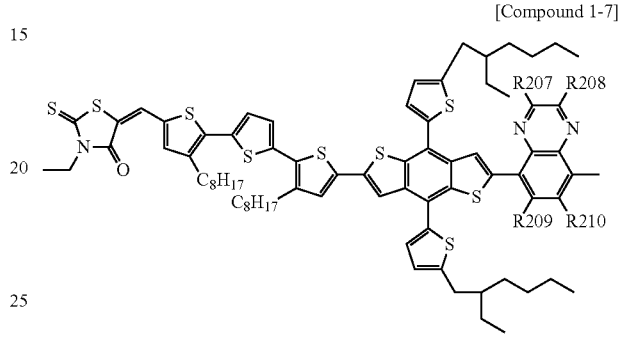
[Compound 1-5]
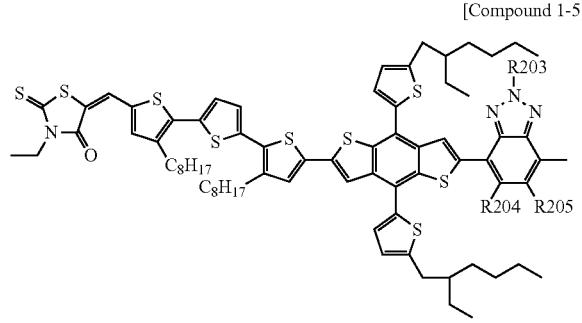
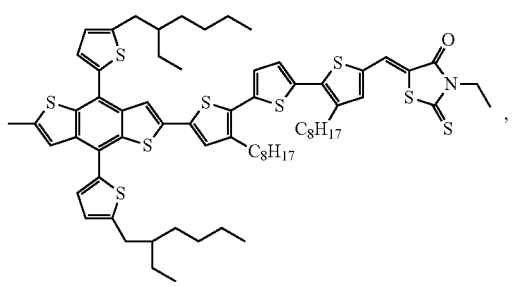
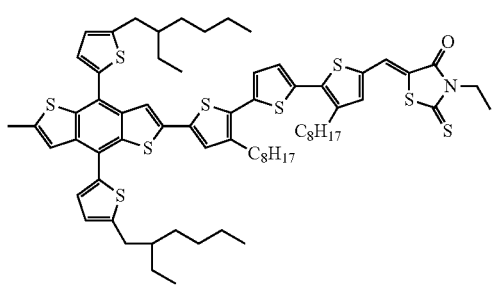
[Compound 1-8]
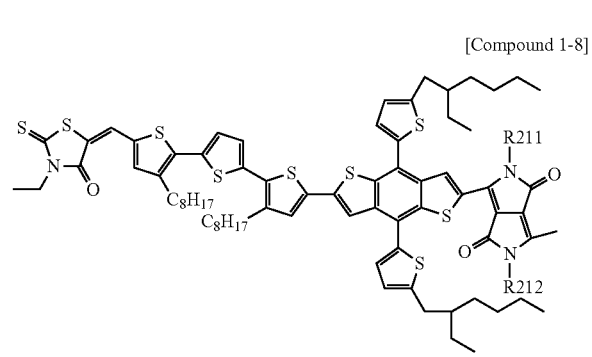
[Compound 1-6]
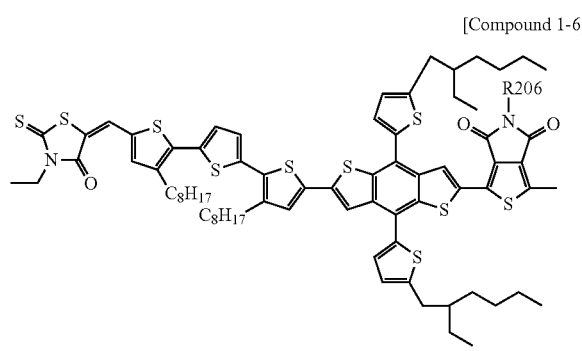
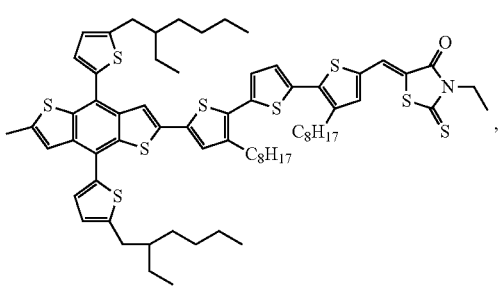

-continued

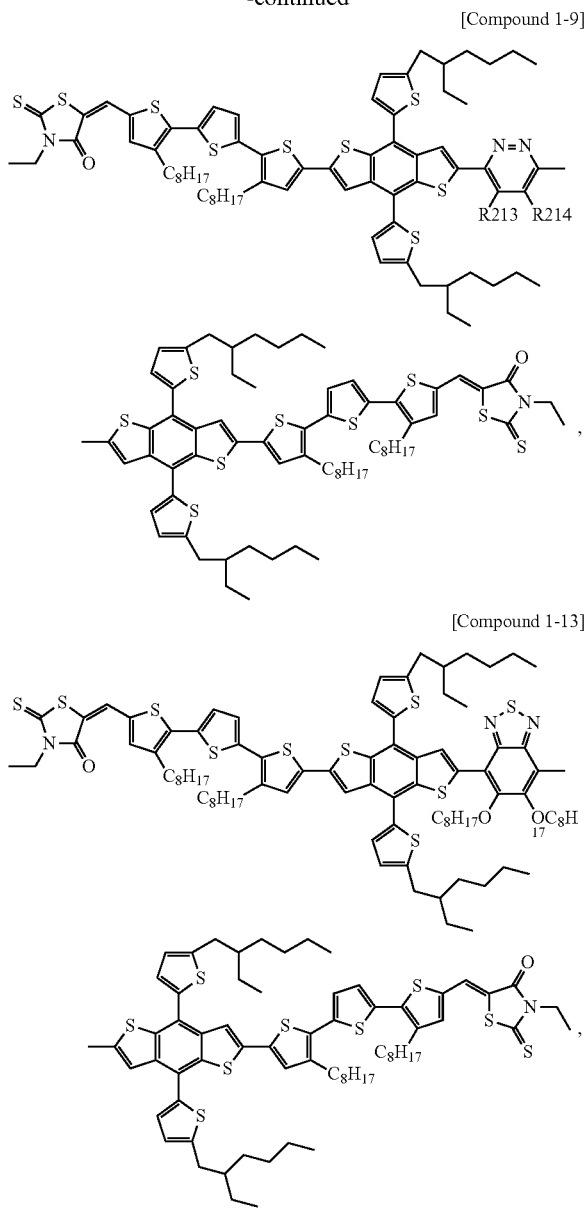

wherein, in Compounds 1-4 to 1-9:
R201 to R214 are the same as or different from each other, and are each independently hydrogen, deuterium, a halogen group, a nitrile group, a nitro group, an imide group, an amide group, a hydroxy group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group comprising one or more of N, O, and S atoms.

2. The heterocyclic compound of claim 1, wherein the heterocyclic compound is a compound of Compound 1-3.

3. The heterocyclic compound of claim 1, wherein the heterocyclic compound is a compound of Compound 1-4 and the definitions of R201 and R202 are the same as in claim 1.

4. The heterocyclic compound of claim 1, wherein the heterocyclic compound is a compound of Compound 1-5 and the definitions of R203, R204, and R205 are the same as in claim 1.

5. The heterocyclic compound of claim 1, wherein the heterocyclic compound is a compound of Compound 1-6 and the definition of R206 is the same as in claim 1.

6. The heterocyclic compound of claim 1, wherein the heterocyclic compound is a compound of Compound 1-7 and the definitions of R207, R208, R209, and R210 are the same as in claim 1.

7. The heterocyclic compound of claim 1, wherein the heterocyclic compound is a compound of Compound 1-8 and the definitions of R211 and R212 are the same as in claim 1.

8. The heterocyclic compound of claim 1, wherein the heterocyclic compound is a compound of Compound 1-9 and the definitions of R213 and R214 are the same as in claim 1.

9. The heterocyclic compound of claim 1, wherein the heterocyclic compound is a compound of Compound 1-13.

10. An organic solar cell comprising:
a first electrode;
a second electrode on the first electrode; and
an organic material layer having one or more layers disposed between the first electrode and the second electrode and comprising a photoactive layer,
wherein the one or more layers of the organic material layer comprise the heterocyclic compound according to claim 1.

11. The organic solar cell of claim 10, wherein the organic material layer comprises a hole transporting layer, a hole injection layer, or a layer which simultaneously transports and injects holes, and
the hole transporting layer, the hole injection layer, or the layer which simultaneously transports and injects holes comprises the heterocyclic compound.

12. The organic solar cell of claim 10, wherein the organic material layer comprises an electron injection layer, an electron transporting layer, or a layer which simultaneously injects and transports electrons, and
the electron injection layer, the electron transporting layer, or the layer which simultaneously injects and transports electrons comprises the heterocyclic compound.

13. The organic solar cell of claim 10, wherein the photoactive layer comprises one or two or more selected from the group consisting of an electron donor and an electron acceptor, and the electron donor comprises the heterocyclic compound.

14. The organic solar cell of claim 13, wherein the electron donor and the electron acceptor constitute a bulk heterojunction (BHJ).

15. The organic solar cell of claim 10, wherein the photoactive layer has a bilayer thin film structure comprising an n-type organic material layer and a p-type organic material layer, and the p-type organic material layer comprises the heterocyclic compound.

* * * * *